US007001792B2

(12) United States Patent
Sauer et al.

(10) Patent No.: US 7,001,792 B2
(45) Date of Patent: Feb. 21, 2006

(54) ULTRA-FAST NUCLEIC ACID SEQUENCING DEVICE AND A METHOD FOR MAKING AND USING THE SAME

(75) Inventors: Jon R. Sauer, Superior, CO (US); Bart J. van Zeghbroeck, Boulder, CO (US)

(73) Assignee: Eagle Research & Development, LLC, Boulder, CO (US)

( * ) Notice: Subject to any disclaimer, the term of this patent is extended or adjusted under 35 U.S.C. 154(b) by 277 days.

(21) Appl. No.: 10/258,439

(22) PCT Filed: Apr. 24, 2001

(86) PCT No.: PCT/US01/13101

§ 371 (c)(1),
(2), (4) Date: Oct. 24, 2002

(87) PCT Pub. No.: WO01/81896

PCT Pub. Date: Nov. 1, 2001

(65) Prior Publication Data

US 2003/0211502 A1    Nov. 13, 2003

Related U.S. Application Data

(63) Continuation-in-part of application No. 09/653,543, filed on Aug. 31, 2000, now Pat. No. 6,413,792.

(60) Provisional application No. 60/259,584, filed on Jan. 4, 2001, provisional application No. 60/217,681, filed on Jul. 12, 2000, provisional application No. 60/199,130, filed on Apr. 24, 2000.

(51) Int. Cl.
*H01L 21/00* (2006.01)

(52) U.S. Cl. .......................... 438/49; 257/253; 435/6; 435/287.2

(58) Field of Classification Search .................. 438/49; 257/253; 422/82.01, 82.02; 435/6, 287.2, 435/287.3, 285.2; 436/89, 151
See application file for complete search history.

(56) References Cited

U.S. PATENT DOCUMENTS

| 3,171,762 A | 3/1965 | Rutz |
| 4,180,771 A | 12/1979 | Guckel |
| 4,209,349 A | 6/1980 | Ho et al. |
| 4,238,757 A | 12/1980 | Schenk |
| 4,256,514 A | 3/1981 | Pogge |
| 4,597,002 A | 6/1986 | Anthony |
| 4,609,932 A | 9/1986 | Anthony |
| 4,656,732 A | 4/1987 | Teng et al. |
| 4,660,063 A | 4/1987 | Anthony |
| 4,764,797 A | 8/1988 | Shaw et al. |
| 4,777,019 A | 10/1988 | Dandekar |
| 4,870,004 A | 9/1989 | Conroy et al. |
| 5,246,879 A | 9/1993 | Hsu et al. |
| 5,466,348 A | 11/1995 | Holm-Kennedy |
| 5,532,128 A | 7/1996 | Eggers et al. |
| 5,556,790 A | 9/1996 | Pettit |
| 5,605,662 A | 2/1997 | Heller et al. |
| 5,632,957 A | 5/1997 | Heller et al. |
| 5,641,634 A | 6/1997 | Mandecki |
| 5,653,939 A | 8/1997 | Hollis et al. |
| 5,654,238 A | 8/1997 | Cronin et al. |
| 5,670,322 A | 9/1997 | Eggers et al. |
| 5,736,332 A | 4/1998 | Mandecki |
| 5,753,967 A | 5/1998 | Lin |
| 5,789,316 A | 8/1998 | Lu |
| 5,795,782 A | 8/1998 | Church et al. |
| 5,827,482 A | 10/1998 | Shieh et al. |
| 5,827,756 A | 10/1998 | Sugino et al. |
| 5,843,767 A | 12/1998 | Beattie |
| 5,846,708 A | 12/1998 | Hollis et al. |
| 5,849,486 A | 12/1998 | Heller et al. |
| 5,868,952 A | 2/1999 | Hatakeyama et al. |
| 5,869,244 A | 2/1999 | Martin et al. |
| 5,871,918 A | 2/1999 | Thorp et al. |
| 5,874,213 A | 2/1999 | Cummins et al. |
| 5,891,630 A | 4/1999 | Eggers et al. |
| 5,945,286 A | 8/1999 | Krihak et al. |
| 5,955,030 A | 9/1999 | Pettit |
| 6,002,131 A | 12/1999 | Manalis et al. |
| 6,015,714 A | 1/2000 | Baldarelli et al. |

| | | | |
|---|---|---|---|
| 6,017,696 A | | 1/2000 | Heller |
| 6,033,980 A | | 3/2000 | Liou et al. |
| 6,040,214 A | | 3/2000 | Boyd et al. |
| 6,046,003 A | | 4/2000 | Mandecki |
| 6,051,380 A | | 4/2000 | Sosnowski et al. |
| 6,054,277 A | | 4/2000 | Furcht et al. |
| 6,057,167 A | | 5/2000 | Shieh et al. |
| 6,060,023 A | | 5/2000 | Maracas |
| 6,060,327 A | | 5/2000 | Keen |
| 6,067,154 A | * | 5/2000 | Hossain et al. .......... 356/237.2 |
| 6,077,773 A | | 6/2000 | Lin |
| 6,087,274 A | | 7/2000 | Tonucci et al. |
| 6,100,014 A | | 8/2000 | Lin et al. |
| 6,133,986 A | | 10/2000 | Johnson |
| 6,150,106 A | | 11/2000 | Martin et al. |
| 6,159,620 A | * | 12/2000 | Heath et al. ................ 428/615 |
| 6,176,990 B1 | | 1/2001 | Yager et al. |
| 6,261,430 B1 | | 7/2001 | Yager et al. |
| 6,413,792 B1 | | 7/2002 | Sauer et al. |
| 6,503,409 B1 | * | 1/2003 | Fleming ...................... 216/56 |
| 6,616,895 B1 | * | 9/2003 | Dugas et al. ............ 422/82.01 |
| 6,627,067 B1 | * | 9/2003 | Branton et al. ............. 205/778 |

FOREIGN PATENT DOCUMENTS

| | | |
|---|---|---|
| WO | 9629593 | 9/1996 |
| WO | 9936573 | 1/1999 |

OTHER PUBLICATIONS

Atkins et al., Chemical Principles, W.H. Freeman: New York, 1999, pp. 196-198, B8, B14.

Stephen Quake, Hazen Babcock, and Steven Chu, "The Dynamics of Partially Extended Single Molecules of DNA", Nature, vol. 388, p. 151-154, Jul. 1997.

S. Tiwari, J.J. Wesler, D.J. DiMaria, and F. Rana, "Currents, Surface Potentials, and Defects Generation in 1.2-1.5 nm Oxide MOSFETs", Proc. Dev. Research Conference, paper II.A-2, Charlottesville, VA, Jun. 1998.

Mark Akeson; Daniel Branton; John J. Kasianowicz; Eric Brandin; and David W. Deamer, "Microsecond Time-Scale Discrimination Among Polycytidylic Acid, Polydenylic Acid, and Polyuridylic Acid as Homopolymers or as Segments within Single RNA Molecules", Biophysical Journal, Dec. 1999, vol. 77, pp. 3227-3233.

H.D. Barber; H.B. Lo; and J.E. Jones, "Repeated Removal of Thin Layers of Silicon by Anodic Oxidation", J. Electrochem. Soc.; Solid-State Science and Technology, Sep. 1976, vol. 123, No. 9, pp. 1405-1409.

Auld et al., "A Neutral Amino Acid Change in Segment IIS4 Dramatically Alters the Gating Properties of the Voltage-Dependent Sodium Channel", 1990, Proc. Natl. Acad. Sci, USA, 87:323-27.

Bensimon, A., et al., "Alignment and Sensitive Detection of DNA by a Moving Interface", 1994, Science, 265:2096-98.

Benz et al., "Mechanism of Sugar Transplant through the Sugar-Specific LamB Channel of Escherichia coli Outer Membrane", 1987, J. Membrane Biol., 100:21-29. Bezrukov et al, "Counting Polymers Moving Through a Single Ion Channel", 1994, Nature, 370: 279-81.

Boulain et al., "Mutagenesis by Random Linker Insertion into the LamB Gene of Escherichia coli K12", 1986, Mol. Gen. Genet., 205:339-48.

Ghadiri et al., "Artificial Transmembrane Ion Channels From Self-Assembling Peptide Nanotubes", 1994, Nature, 369:301-304.

Hall et al., "Alamethicin: A Rich Model for Channel Behavior", 1984, J. Biophys., 45:233-47.

Harrington et al., "The F Pilus of Escherichia coli Appears to Support Stable DNA Transfer in the Absence of Wall-to-Wall Contact Between Cells", 1990, J. Bacteriology, 172 (19):7263-64.

Heinemann et al., "Open Channel Noise IV: Estimation of Rapid Kinetics of Formamide Block in Gramicidin A Channels", 1988, J. Biophys., 54:757-64.

Heinemann et al., "Open Channel Noise V: Fluctuating Barriers to Ion Entry in Gramicidin A Channels", 1990, J. Biophys., 57:499-514.

Henry et al., "Blockade of a Mitochondrial Cationic Channel by an Addressing Peptide: An Electrophysiological Study", 1989, J. Membranee Biol., 112:139-47.

Hoshi et al., "Biophysical and Molecular Mechanisms of Shaker Potassium Channel Inactivation", 1990, Science, 250:533-38.

Hoshi et al., "Two Types of Inactivation in Shaker $K^+$Channels: Effects of Alternations in the Carboxy-Terminal Region", 1991, Neuron, 7:547-56.

Kubitschek, "Electronic Counting and Sizing of Bacteria", Nature, 1958, 182:234-35.

Lakey et al., "The Voltage-Dependent Activity of Escherichia coli Porins in Different Planar Bilayer Reconstitutions", 1989, Eur. J. Biochem., 186:303-308.

Hamill et al. "Improved Patch-Clamp Techniques for High-Resolution Current Recording from Cells and Cell-Free Membrane Patches", 1981, Pflugers Archiv. Eur. J. Physiology, 39(2):85-100.

Lopez et al., "Hydrophobic Substitution Mutations in the S4 Sequence Alter Voltage-Dependent Gating in Shaker $K^+$ Channels", 1991, Neuron, 7:327-36.

Moellerfeld et al. "Improved Stability of Black Lipid Membranes by Coating with Polysaccharide Derivatives Bearing Hydrophibic Anchor Groups", 1986, Biochimica et Biophysica Acta, 857:265-70.

Nath et al., "Transcription by T7 RNA Polymerase Using benzo [a] pyrene-modified templates", 1991, Carcinogenesis, 12(6):973-76.

Neher et al., "Single-Channel Currents Recorded from Membrane of Denervated Frog Muscle Fibres", 1976, Nature, 260:799-801.

Novick et al., "Fluorescence Measurement of the Kinetics of DNA Injection by Bacteriophage 1 into Liposomes", 1988, Biochemistry, 27:7919-24.

Ollis et al., "Domain of E. coli DNA Polymerase I Showing Sequence Homology to T7 DNA Polymerase", 1985, Nature, 313:818-19.

Ollis et al., Structure of Large Fragment of Escherichia coli DNA Polymerase I Complexed with "TMP", 1985, Nature, 313:762-66.

Patton et al., "Amino Acid Residues Required for Fast $N^+$-channel Inactivation: Charge Neutralizations and Deletions in the III-IV Linker", 1992, Proc. Natl. Acad. Sci. USA 89:10905-909.

Shiver et al., "On the Explanation of the Acidic pH Requirement for In Vitro Activity of Colicin E1", 1987, J. Biological Chem., 262(29):14273-281.

Sigworth et al., "Open Channel Noise: III. High Resolution Recordings Show Rapid Current Fluctations in Gramicidin A and Four Chemical Analogues", 1987, J. Biophys., 52: 1055-64.

Simon et al., "A Protein Conducting Channel in the Endoplasmic Reticulum", Cell, 65:371-80, (1991).

Taylor et al., "Reversed Alamethicin Conductance in Lipid Bilayers", 1991, J. Biophys., 59:873-79.

Weiss et al., "Molecular Architecture and Electrostatic Properties of a Bacterial Porin", 1991, Science, 254:1627-30.

West et al., "A Cluster of Hydrophobic Amino Acid Residues Required for Fast Na+-channel Inactivation", 1992, Proc. Natl. Acad. Sci. USA, 89:10910-14.

Wonderlin et al., "Optimizing Planar Lipid Bilayer Single-Channel Recordings for High Resolution with Rapid Voltage Steps", 1990, J. Biophys., 58:289-97.

Dargent et al., "Selectivity for Maltose and Maltodextrins of Maltoporin, a Pore-Forming Protein of E. Coli Outer Membrane", 1987, FEB Letters, 220(1):136-42.

Dargent et al., "Effect of Point Mutations on the in-Vitro Pore Properties of Maltoporin, a Protein of *Escherichia coli* Outer Membrane", 1988, J. Mol. Biol. 201:497-506.

DeBlois et al., "Electrokinetic Measurements with Submicron Particles and Pores by the Resistive Pulse Technique", 1977, J. Colloid and Interface Science, 61(2): 323-35.

Ehrmann et al., "Genetic Analysis of Membrane Protein Topology by a Sandwich Gene Fusion Approach", 1990, Proc. Natl. Acad. Sci. USA, 87:7574-78.

Ferenci et al., "Channel Architecture in Maltoporin: Dominance Studies with LamB Mutations Influencing Maltodextrin Binding Provide Evidence for Independent Selectivity Filters in Each Subunit", 1989, J. Bacteriology 171(2):855-61.

Sergey M. Bezrukov; Igor Vodyanoy; and V. Adrian Parseglan, "Counting Polymers Moving Through a Single Ion Channel", Letters to Nature, Jul. 28, 1994, vol. 370, pp. 279-281.

Wen-Hwa Chu, Member, IEEE, Ruby Chin, Tony Huen, Member, IEEE and Mauro Ferrari, "Silicon Membrane Nanofilters from Sacrificial Oxide Removal", Journal of Microelectromechnical Systems, Mar. 1, 1999, vol. 8, pp. 34-42.

Roger H. Schneider, Samuel J. Dwyer III, "Medical Imaging II: Image Formation, Detection, Processing, and Interpretation", SPIE-The International Society for Optical Engineering, vol. 914 (Part A), Medical Imagining II (1988), pp. 512-517.

Branton et al., "Purine and Pryimidine Nucleic Acids Produce Distinctive Current Blockages in the Alpha Hemolysin Pore", Akeson Biophysical Journal, v. 76, No. 1, part 2 of 2, paper M-PM-C7, p. A172, Jan. 1999.

Hayashi A.M., Semicondutors—New Silicon Tricks, Scientific American, 278:(1), 44-45, Jan. 1998.

Cees Dekker, "Carbon Nanotubes as Molecular Quantum Wires", Physics Today, p. 22, May 1999.

Binning G.K., "The Scanning Tunneling Microscope", Binning G.K., Rohrer H., Scientific American, 253:(2), 50-& 1985; "Atomic-Force Microscopy", Physica Scripta, T19A, 53-54, 1987.

Gerstein and Levitt, "Stimulating Water and the Molecules of Life", Scientific American, p. 100, Nov. 1998.

Kasianowicz, J.J., Akeson, M., Henrickson, S.E., Bazrukov, S.M., Brandin E., Branton, D. Damer, D.W., "Charged and Neutral Polymer Transport in a Single Ionic Channel", Abstract of papers of the American Chemical Society 1998, vol. 216, pp. 263-PHYS.

Boulanger et al., "Characterization of Ion Channels Involved in the Penetration of Phage T4 DNA into *Escherichia coli* Cells", 1988, J. Biolog. Chem., 263(20):9767-75.

Boulanger et al., "Ion Channels Are Likely to Be Involved in the Two Steps of Phage T5 DNA Penetration into *Escherichia coli* Cells", 1992, J. Biolog. Chem., 267(5): 3168-72.

Boyd et al., "Determinants of Membrane Protein Topology", 1987, Proc. Natl. Acad. Sci. USA, 84:8525-29.

Charbit et al., "Permissive Sites and Topology of an Outer Membrane Protein with a Reporter Epitope", 1991, J. Bacteriology, 173(1):262-75.

J.J. Kasianowicz, E. Brandin, D. Branton, and D.W. Deamer, "Characterization of Individual Polynucleotide Molecules Using a Membrane Channel", Proc. Nat'l. Acad. Sci. USA. 93: 13770-13773, Nov., 1996.

Richard A. Kiehl, "Single-Electron Device Research: Some Directions and Challenges," Solid State and Photonics Laboratory Stanford, California. 94305-4075, Jun. 1999.

* cited by examiner

*Primary Examiner*—Jack Chen
(74) *Attorney, Agent, or Firm*—Roylance, Abrams, Berdo & Goodman, LLP

(57) ABSTRACT

A system and method employing at least one semiconductor device, or an arrangement of insulating and metal layers, having at least one detecting region which can include, for example, a recess or opening therein, for detecting a charge representative of a component of a polymer, such as a nucleic acid strand, proximate to the detecting region, and a method for manufacturing such a semiconductor device. The system and method can thus be used for sequencing individual nucleotides or bases of ribonucleic acid (RNA) or deoxyribonucleic acid (DNA). The semiconductor device includes at least two doped regions, such as two n-typed regions implanted in a p-typed semiconductor layer or two p-typed regions implanted in an n-typed semiconductor layer. The detecting region permits a current to pass between the two doped regions in response to the presence of the component of the polymer, such as a base of a DNA or RNA strand. The current has characteristics representative of the component of the polymer, such as characteristics representative of the detected base of the DNA or RNA strand.

5 Claims, 16 Drawing Sheets

ULTRA-FAST NUCLEIC ACID SEQUENCING DEVICE AND A METHOD FOR MAKING AND USING THE SAME

This is a continuation-in-part of U.S. patent application Ser. No. 09/653,543, filed on Aug. 31, 2000, now U.S. Pat. No. 6,413,792.

The present application claims benefit under 35 U.S.C. § 119(e) of a provisional U.S. Patent Application of Jon R. Sauer et al. entitled "Ultra-Fast, Semiconductor-Based Gene Sequencing", Ser. No. 60/199,130, filed Apr. 24, 2000, of a provisional U.S. Patent Application of Bart Van Zeghbroeck et al. entitled "Charge Sensing and Amplification Device for DNA Sequencing", Ser. No. 60/217,681, filed Jul. 12, 2000, and of a provisional U.S. Patent Application of Jon R. Sauer et al. entitled "Charge Sensing and Amplification Device for DNA Sequencing, Ser. No. 60/259,584, filed Jan. 4, 2001, and claims benefit under 35 U.S.C. § 120 of a non-provisional U.S. patent application of Jon R. Sauer et al. entitled "An Ultra-Fast Nucleic Acid Sequencing Device and a Method for Making and Using the Same", Ser. No. 09/653, 543, filed Aug. 31, 2000, of which the present application is a continuation-in-part, the entire contents of all of said provisional applications and said non-provisional application being incorporated herein by reference.

BACKGROUND OF THE INVENTION

1. Field of the Invention

The present invention relates to a system and method employing a semiconductor device having a detecting region for identifying the individual mers of long-chain polymers, such as carbohydrates and proteins, as well as individual bases of deoxyribonucleic acid (DNA) or ribonucleic acid (RNA), and a method for making the semiconductor device. More particularly, the present invention relates to a system and method employing a semiconductor device, similar to a field-effect transistor device, capable of identifying the bases of a DNA/RNA strand to thus enable sequencing of the strand to be performed.

2. Description of the Related Art

DNA consists of two very long, helical polynucleotide chains coiled around a common axis. The two strands of the double helix run in opposite directions. The two strands are held together by hydrogen bonds between pairs of bases, consisting of adenine (A), thymine (T), guanine (G), and cytosine (C). Adenine is always paired with thymine, and guanine is always paired with cytosine. Hence, one strand of a double helix is the complement of the other.

Genetic information is encoded in the precise sequence of bases along a DNA strand. In normal cells, genetic information is passed from DNA to RNA. Most RNA molecules are single stranded but many contain extensive double helical regions that arise from the folding of the chain into hairpin-like structures.

Mapping the DNA sequence is part of a new era of genetic-based medicine embodied by the Human Genome Project. Through the efforts of this project, one day doctors will be able to tailor treatment to individuals based upon their genetic composition, and possibly even correct genetic flaws before birth. However, to accomplish this task it will be necessary to sequence each individual's DNA. Although the human genome sequence variation is approximately 0.1%, this small variation is critical to understanding a person's predisposition to various ailments. In the near future, it is conceivable that medicine will be "DNA personalized", and a physician will order sequence information just as readily as a cholesterol test is ordered today. Thus, to allow such advances to be in used in everyday life, a faster and more economical method of DNA sequencing is needed.

One method of performing DNA sequencing is disclosed in U.S. Pat. No. 5,653,939, the entire content of which is incorporated herein by reference. This method employs a monolithic array of test sites formed on a substrate, such as a semiconductor substrate. Each test site includes probes which are adapted to bond with a predetermined target molecular structure. The bonding of a molecular structure to the probe at a test site changes the electrical, mechanical and optical properties of the test site. Therefore, when a signal is applied to the test sites, the electrical, mechanical, or optical properties of each test site can be measured to determine which probes have bonded with their respective target molecular structure. However, this method is disadvantageous because the array of test sites is complicated to manufacture, and requires the use of multiple probes for detecting different types of target molecular structures.

Another method of sequencing is known as gel electrophoresis. In this technology, the DNA is stripped down to a single strand and exposed to a chemical that destroys one of the four nucleotides, for example A, thus producing a strand that has a random distribution of DNA fragments ending in A and labeled at the opposite end. The same procedure is repeated for the other three remaining bases. The DNA fragments are separated by gel electrophoresis according to length. The lengths show the distances from the labeled end to the known bases, and if there are no gaps in coverage, the original DNA strand fragment sequence is determined.

This method of DNA sequencing has many drawbacks associated with it. This technique only allows readings of approximately 500 bases, since a DNA strand containing more bases would "ball" up and not be able to be read properly. Also, as strand length increases, the resolution in the length determination decreases rapidly, which also limits analysis of strands to a length of 500 bases. In addition, gel electrophoresis is very slow and not a workable solution for the task of sequencing the genomes of complex organisms. Furthermore, the preparation before and analysis following electrophoresis is inherently expensive and time consuming. Therefore, a need exists for a faster, consistent and more economical means for DNA sequencing.

Another approach for sequencing DNA is described in U.S. Pat. Nos. 5,795,782 and 6,015,714, the entire contents of which are incorporated herein by reference. In this technique, two pools of liquid are separated by a biological membrane with an alpha hemolysin pore. As the DNA traverses the membrane, an ionic current through the pore is blocked. Experiments have shown that the length of time during which the ionic current through the pore is blocked is proportional to the length of the DNA fragment. In addition, the amount of blockage and the velocity depend upon which bases are in the narrowest portion of the pore. Thus, there is the potential to determine the base sequence from these phenomena.

Among the problems with this technique are that individual nucleotides cannot, as yet, be distinguished. Also, the spatial orientation of the individual nucleotides is difficult to discern. Further, the electrodes measuring the charge flow are a considerable distance from the pore, which adversely affects the accuracy of the measurements. This is largely because of the inherent capacitance of the current-sensing electrodes and the large statistical variation in sensing the small amounts of current. Furthermore, the inherent shot noise and other noise sources distort the signal, incurring additional error. Therefore, a need exists for a more sensitive detection system which discriminates among the bases as they pass through the sequencer.

SUMMARY OF THE INVENTION

An object of the present invention is to provide a system and method for accurately and effectively identifying individual bases of DNA or RNA.

Another object of the present invention is to provide a system and method employing a semiconductor device for sequencing individual bases of DNA or RNA.

A further object of the present invention is to provide a method for manufacturing a semiconductor-based DNA or RNA sequencing device.

Another object of the present invention is to provide a system and method for accurately and effectively identifying the individual mers of long-chain polymers, such as carbohydrates or proteins, as well as measuring the lengths of the long-chain polymers.

Still another object of the present invention is to provide a system and method employing a semiconductor-based device having an opening therein, for accurately and effectively identifying bases of DNA or RNA by measuring charge at a location where the DNA or RNA molecules traverse the opening in the sequencer, to thus eliminate or at least minimize the effects of shot noise and other noise sources associated with the random movement of the DNA or RNA molecules through the opening.

These and other objects of the invention are substantially achieved by providing a system for detecting at least one polymer, comprising at least one semiconductor device, or an arrangement of insulating and metal layers, having at least one detecting region which is adapted to detect a charge representative of a component of the polymer proximate to the detecting region. The component can include a base in a nucleic acid strand, so that the detecting region is adapted to detect the charge which is representative of the base in the nucleic acid strand. The detecting region is further adapted to generate a signal representative of the detected charge. Also, the detecting region can include a region of the semiconductor device defining a recess in the semiconductor device, or an opening in the semiconductor device having a cross-section sufficient to enable the polymer to enter the opening, so that the detecting region detects the charge of the component in the opening. Furthermore, the semiconductor device preferably further includes at least two doped regions, and the detecting region can pass a current between the two doped regions in response to a presence of the component proximate to the detecting region.

The above and other objects of the invention are also substantially achieved by providing a method for detecting at least one polymer, comprising the steps of positioning a portion of the polymer proximate to a detecting region of at least one semiconductor device, and detecting at the detecting region a charge representative of a component of the polymer proximate to the detecting region. The component can include a base in a nucleic acid strand, so that the detecting step detects a charge representative of the base. The method further comprises the step of generating at the detecting region a signal representative of the detected charge. The detecting region can include a region of the semiconductor device defining a recess in the semiconductor device, or an opening in the semiconductor device having a cross-section sufficient to enable the polymer to enter the opening, so that the detecting step detects the charge of the component in the recess or opening. Furthermore, the semiconductor device can further include at least two doped regions, so that the method can further include the step of passing a current between the two doped regions in response to a presence of the component proximate to the detecting region.

The above and other objects of the invention are further substantially achieved by providing a method for manufacturing a device for detecting a polymer, comprising the steps of providing a semiconductor structure comprising at least one semiconductor layer, and creating a detecting region in the semiconductor structure, such that the detecting region is adapted to detect a charge representative of a component of the polymer proximate to the detecting region. The component can include a base in a nucleic acid strand, and the detecting region can be created to detect a charge representative of the base in the nucleic acid strand. The method can further include the step of creating a recess in the semiconductor structure, or creating an opening in the semiconductor structure having a cross-section sufficient to enable a portion of the polymer to pass therethrough, and being positioned in relation to the detecting region such that the detecting region is adapted to detect the charge representative of the component in the recess or opening. The method can further include the step of forming an insulating layer on a wall of the semiconductor layer having the opening to decrease the cross-section of the opening. Furthermore, the method can include the step of creating at least two doped regions in the semiconductor layer which are positioned with respect to the detecting region such that the detecting region is adapted to pass a current between the doped regions in response to the component of the polymer proximate to the detecting region. The doped regions can be separated by a portion of the semiconductor layer having a different doping, and can be created as a stack of doped regions, each having a first doping and being separated by a layer having a second doping. The doped regions can include either a p-type or an n-type doping.

BRIEF DESCRIPTION OF THE DRAWINGS

These and other objects, advantages and novel features of the invention will be more readily appreciated from the following detailed description when read in conjunction with the accompanying drawings, in which.

DETAILED DESCRIPTION OF THE PREFERRED EMBODIMENTS

Figure 1:
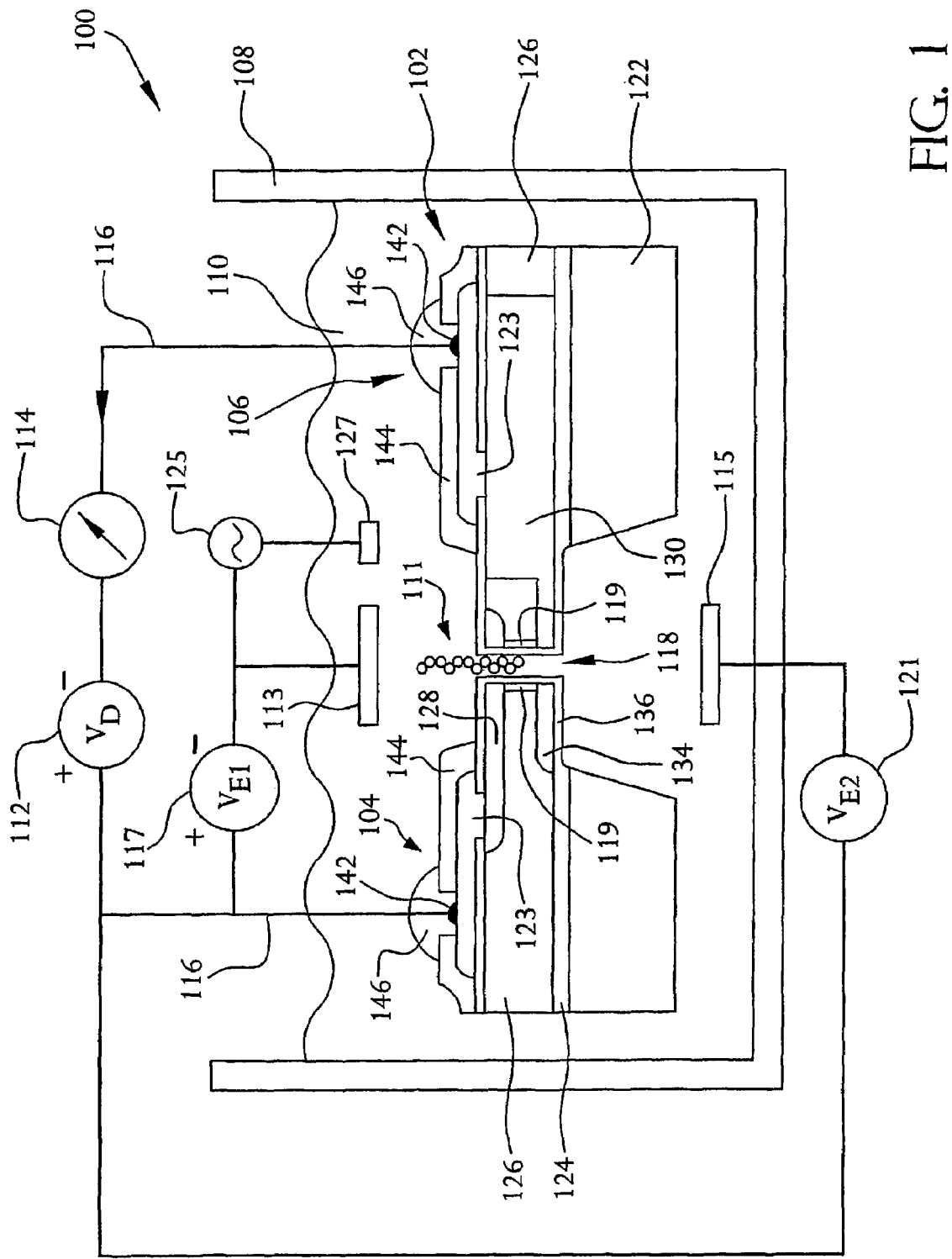
FIG. 1 illustrates a system for performing DNA or RNA sequencing comprising a DNA or RNA sequencer constructed in accordance with an embodiment of the present invention.
Figure 2:
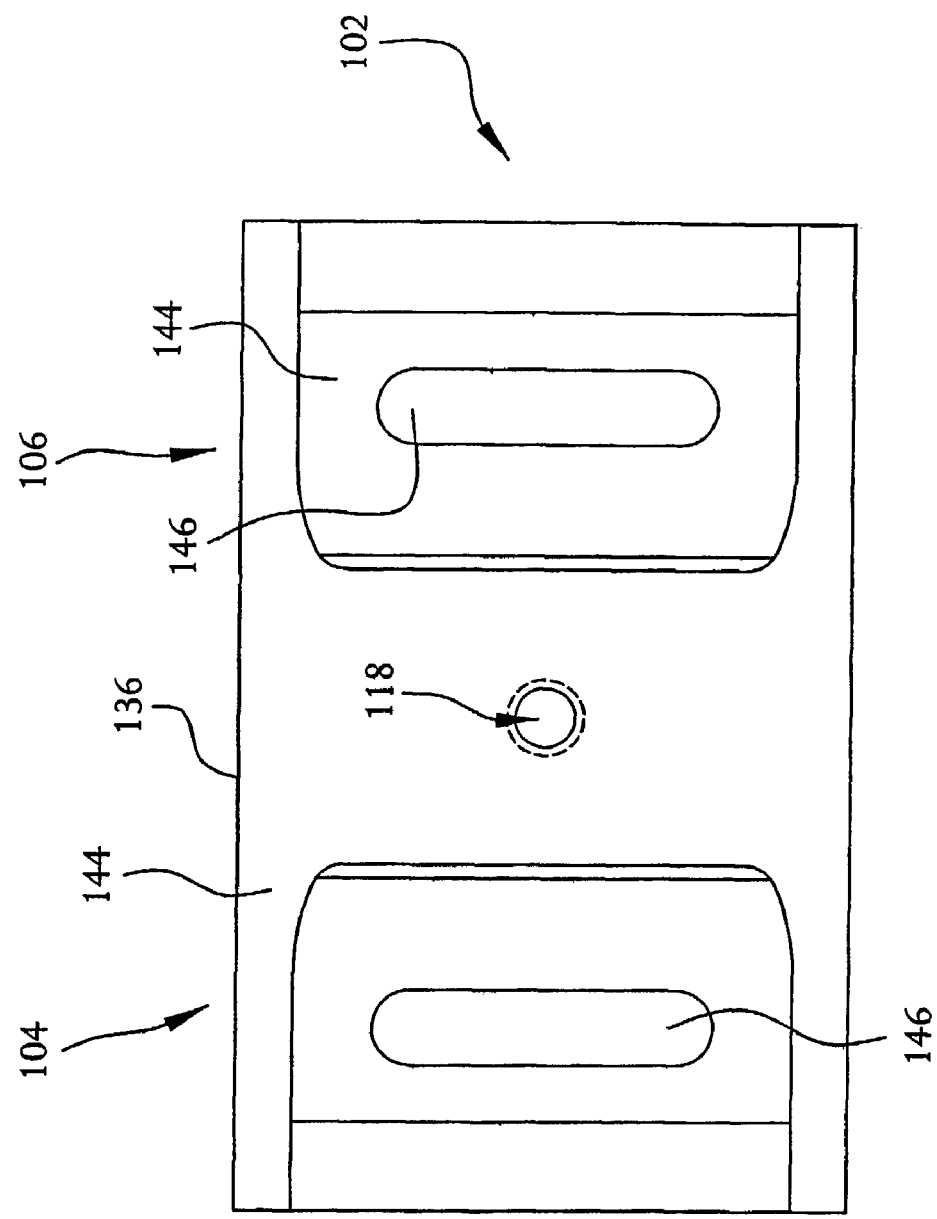
FIG. 2 illustrates a top view of the DNA or RNA sequencer shown in FIG. 1.

FIGS. 1 and 2 illustrate a system 100 for detecting the presence of a polymer, such as DNA or RNA, a protein or carbohydrate, or a long chain polymer such as petroleum, and, more preferably, for identifying the individual mers of the polymer or long chain polymer, as well as the length of the polymer or long chain polymer. The system 100 is preferably adaptable for performing sequencing of nucleic acids, such as DNA or RNA sequencing, according to an embodiment of the present invention. Accordingly, for purposes of this description, the system 100 will be discussed in relation to nucleic acid sequencing.

The system 100 includes a nucleic acid sequencing device 102 which, as described in more detail below, is a semiconductor device. Specifically, the nucleic acid sequencing device 102 resembles a field-effect transistor, such as a MOSFET, in that it includes two doped regions, a drain region 104 and a source region 106. However, unlike a MOSFET, the nucleic acid sequencing device does not include a gate region for reasons discussed below.

The nucleic acid sequencing device 102 is disposed in a container 108 that includes a liquid 110 such as water, gel, a buffer solution such as KCL, or any other suitable solution. It is important to note that the solution 110 can be an insulating medium, such as oil, or any other suitable insulating medium. In addition, the container 108 does not need to include a medium such as a liquid. Rather, the container 108 can be sealed and evacuated to create a vacuum in which nucleic acid sequencing device 102 is disposed. Also, although FIG. 1 shows only a single nucleic acid sequencing device 102 in the container 108 for exemplary purposes, the container can include multiple nucleic acid sequencing devices 102 for performing multiple DNA sequencing measurements in parallel.

The liquid 110 or other medium or vacuum in container 108 includes the nucleic acid strands or portions of nucleic acid strands 111 to be sequenced by nucleic acid sequencing device 102. As further shown, voltage source 112, such as a direct current voltage source, is coupled in series with a current meter 114 by leads 116 across drain and source regions 104 and 106, respectively. In this example, the positive lead of voltage source 112 is coupled to the drain region 104 while the negative lead of voltage source 112 is coupled via the current meter 114 to source region 106.

The voltage potential applied across drain and source regions 104 and 106 of nucleic acid sequencing device 102 can be small, for example, about 100 mV, which is sufficient to create a gradient across drain and source regions 104 and 106, to draw the nucleic acid strands into opening 118 of the nucleic acid sequencing device 102. That is, the nucleic acid strands 111 move through the opening 118 because of the local gradient. Alternatively or in addition, the liquid can include an ionic solution. In this event, the local gradient causes the ions in the solution to flow through the opening 118, which assists the nucleic acid strands 111, such as DNA or RNA, to move through the opening 118 as well.

Additional electrodes 113 and 115 positioned in the medium 110 and connected to additional voltage sources 117 and 121 would further facilitate the movement of the nucleic acid strands towards the opening 118. In other words, the external electrodes 113 and 115 are used to apply an electric field within the medium 110. This field causes all of the charged particles, including the nucleic acid strand 111, to flow either toward the opening 118 or away from the opening 118. Thus electrodes 113 and 115 are used as a means to steer the nucleic acid strands 111 into or out of the opening 118. In order to connect voltage sources 112 and 117 to the nucleic acid sequencer 102, metal contacts 123 are coupled to the n-type doped region 128 and 130, described in more detail below. The electrodes 113 and 115 could also provide a high frequency voltage which is superimposed on the DC voltage by an alternating voltage source 125. This high frequency voltage, which can have a frequency in the radio frequency range, such as the megahertz range (e.g., 10 MHz), causes the nucleic acid strand 111 and ions to oscillate. This oscillation makes passage of the nucleic acid strand 111 through the opening 118 smoother, in a manner similar to shaking a salt shaker to enable the salt grains to pass through the openings in the shaker. Alternatively, a device 127, such as an acoustic wave generator, can be disposed in the liquid 110 or at any other suitable location, and is controlled to send sonic vibrations through the device 102 to provide a similar mechanical shaking function.

As can be appreciated by one skilled in the art, the nucleic acid strands each include different combinations of bases A, C, G and T, which each contain a particular magnitude and polarity of ionic charge. The charge gradient between drain and source regions 104 and 106, or otherwise across the opening 118, will thus cause the charged nucleic acid strands to traverse the opening 118. Alternatively, another voltage source (not shown) can be used to create a difference in voltage potential between the opening 118 and the liquid. Also, a pressure differential can be applied across the opening 118 to control the flow of the DNA independent from the voltage applied between the source and drain 104 and 106.

In addition, the Sequencing device 102 can attract the nucleic acid strands to the opening 118 by applying a positive voltage to the medium 110 relative to the voltage source 112. Furthermore, the nucleic acid strands in the medium 110 can be pushed in and out of the opening 118 and be analyzed multiple times by reversing the polarity across drain and source regions 104 and 106, respectively.

As described in more detail below, the opening 118 is configured to have a diameter within the nanometer range, for example, within the range of about 1 nm to about 10 nm. Therefore, only one DNA strand can pass through opening 118 at any given time. As a DNA strand passes through opening 118, the sequence of bases induce image charges which form a channel 119 between the drain and source regions 104 and 106 that extends vertically along the walls of the device defining opening 118. As a voltage is applied between the source 136 and drain 128 by means of the voltage source 112, these image charges in the channel flow from source to drain, resulting in a current flow which can be detected by the current meter 114. The current exists in the channel as long as the charge is present in the opening 118, and thus the device current detected by the current meter 114 is much larger than the current associated with the moving charge. For example, a singly charged ion passing through the opening 118 in one microsecond accounts for an ion current of 0.16 pA and a device current of 160 nA.

Alternatively, the bases induce a charge variation in channel 119, leading to a current variation as detected by current meter 114. Any variation of the ion flow through the opening due to the presence of the DNA strand would also cause a variation to the image charge in the channel 119 and results in a current variation as detected by current meter 114. That is, the device current measured by current meter 114 will diminish from, for example, 80 $\mu$A to 4 $\mu$A. as the DNA strand 111 passes through opening 118.

Each different type of bases A, C, G, and T induces a current having a particular magnitude and waveform representative of the particular charge associated with its respective type of bases. In other words, an A type base will induce a current in a channel between the drain and source regions of the nucleic acid sequencing device 102 having a magnitude and waveform indicative of the A type base. Similarly, the C, T and G bases will each induce a current having a particular magnitude and waveform.

Figure 3:
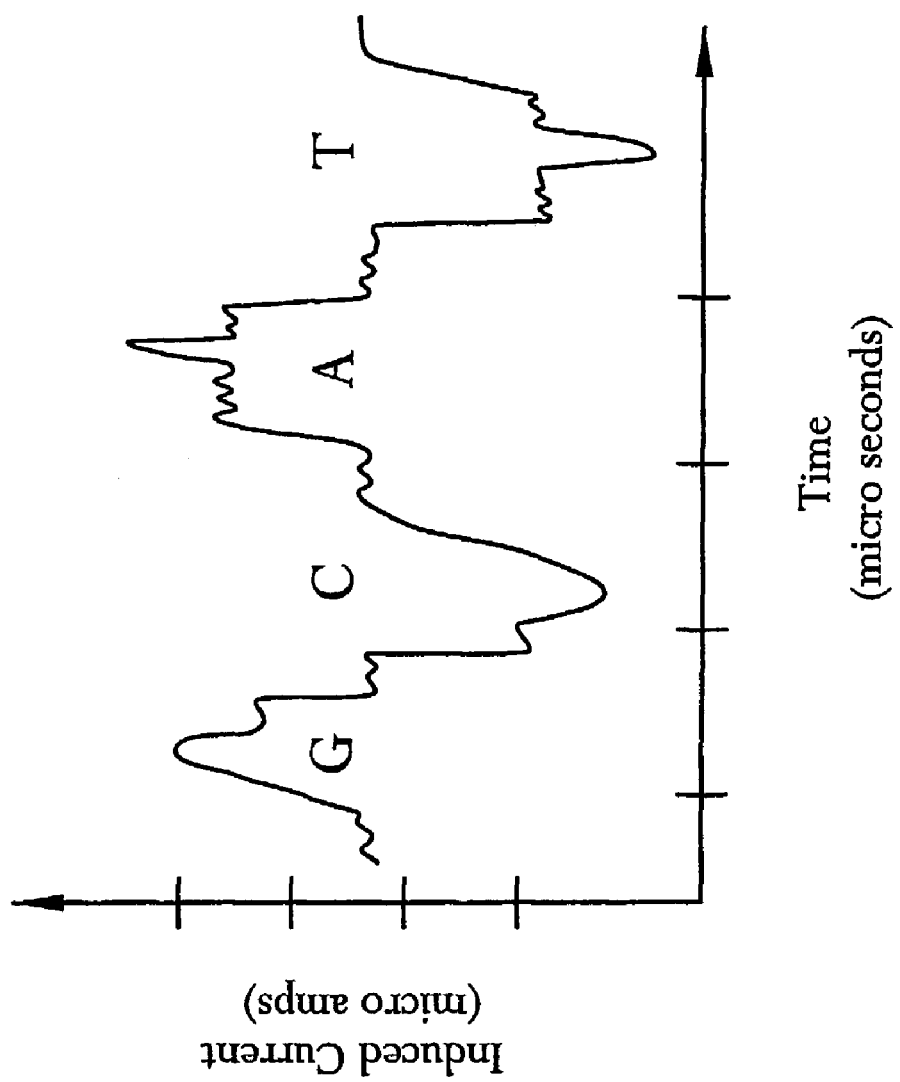
FIG. 3 is a graph showing an example of the waveform representing the current detected by a current detector in the system shown in FIG. 1 as the adenine (A), thymine (T), guanine (G), and cytosine (C) bases of a DNA or RNA sequence pass through the DNA or RNA sequencer.

An example of a waveform of the detected current is shown in FIG. 3, which symbolically illustrates the shape, magnitude, and time resolution of the expected signals generated by the presence of the A, C, G and T bases. The magnitude of current is typically in the microampere ($\mu$A) range, which is a multiplication factor of $10^6$ greater than the ion current flowing through the opening 118, which is in the picoampere range. A calculation of the electrostatic potential of the individual bases shows the complementary distribution of charges that lead to the hydrogen bonding. For example, the T-A and C-G pairs have similar distributions when paired viewed from the outside, but, when unpaired, as would be the case when analyzing single-stranded DNA, the surfaces where the hydrogen bonding occurs are distinctive. The larger A and G bases are roughly complementary (positive and negative reversed) on the hydrogen bonding surface with similar behavior for the smaller T and C bases.

Accordingly, as the DNA strand passes through opening 118, the sequence of bases in the strand can be detected and thus ascertained by interpreting the waveform and magnitude of the induced current detected by current meter 114. The system 100 therefore enables DNA sequencing to be performed in a very accurate and efficient manner.

Since the velocity of the electrons in the channel 119 is much larger than the velocity of the ions passing through the opening, the drain current is also much larger than the ion current through the opening 118. For an ion velocity of 1 cm/s and an electron velocity of $10^6$ cm/s, an amplification of 1 million can be obtained.

Also, the presence of a DNA molecule can be detected by monitoring the current $I_P$ through the opening 118. That is, the current $I_P$ through the opening reduces from 80 pA to 4 pA when a DNA molecule passes through the opening. This corresponds to 25 electronic charges per microsecond as the molecule passes through the opening.

Measurement of the device current rather than the current through the opening has the following advantages. The device current is much larger and therefore easier to measure. The larger current allows an accurate measurement over a short time interval, thereby measuring the charge associated with a single DNA base located between the two n-type regions. In comparison, the measurement of the current through the opening has a limited bandwidth, limited by the shot-noise associated with the random movement of charge through the opening 118. For example, measuring a 1 pA current with a bandwidth of 10 MHz yields an equivalent noise current of 3.2 pA. Also, the device current can be measured even if the liquids on both sides of the opening 118 are not electrically isolated. That is, as discussed above, the sequencing device 102 is immersed in a single container of liquid. Multiple sequencers 102 can thus be immersed in a single container of liquid, to enable multiple current measurements to be performed in parallel. Furthermore, the nanometer-sized opening 118 can be replaced by any other structure or method which brings the DNA molecule in close proximity to the two n-type regions, as discussed in more detail below.

Figure 4:
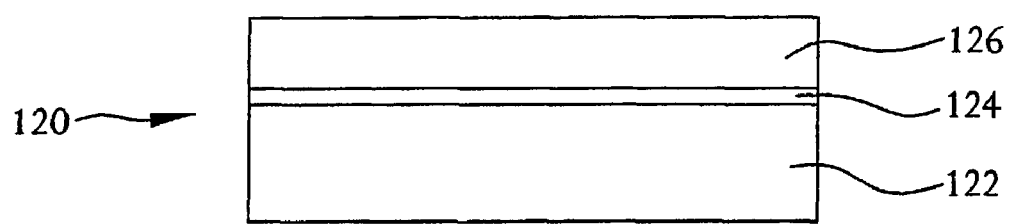
FIG. 4 illustrates a cross-sectional view of a silicon-on-insulator (SOI) substrate from which a DNA or RNA sequencer as shown in FIG. 1 is fabricated in accordance with an embodiment of the present invention.

The preferred method of fabricating a nucleic acid sequencing device 102 will now be described with reference to FIGS. 4–16. As shown in FIG. 4, the fabrication process begins with a wafer 120, such as a silicon-on-insulator (SOI) substrate comprising a silicon substrate 122, a silicon dioxide (SiO$_2$) layer 124, and a thin layer of p-type silicon 126. In this example, the silicon substrate 122 has a thickness within the range of about 300 $\mu$m to about 600 $\mu$m, the silicon dioxide layer 124 has a thickness within the range of about 200 to 6400 mn, and the p-type silicon layer 126 has a thickness of about 1 μm or less (e.g., within a range of about 10 nm to about 1000 mn).

Figure 5:
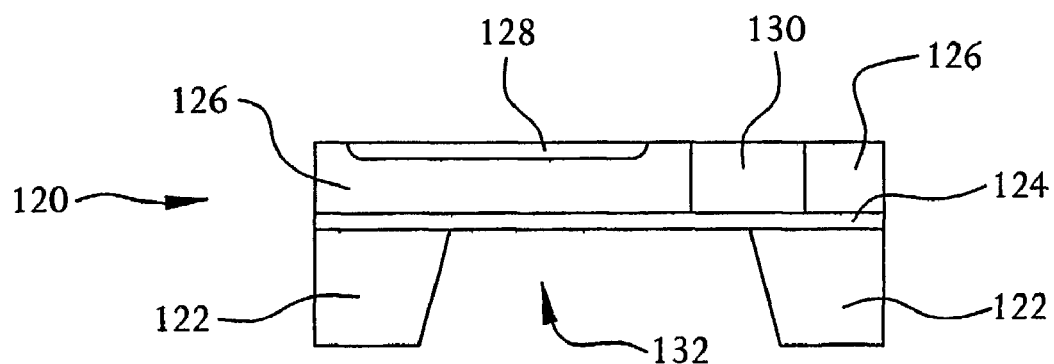
FIG. 5 illustrates a cross-sectional view of the SOI substrate shown in FIG. 5 having shallow and deep n-type regions formed in the silicon layer, and a portion of the substrate etched away.

As shown in FIG. 5, a doped n-type region 128 is created in the p-type silicon layer 126 by ion implantation, and annealing or diffusion of an n-type dopant, such as arsenic, phosphorous or the like. As illustrated, the n-type region 128 is a shallow region which does not pass entirely through p-type silicon 126. A deep n-type region 130 is also created in the p-type silicon 126 as illustrated in FIG. 5. The deep n-type region 130 passes all the way through the p-type silicon 126 to silicon dioxide 124 and is created by known methods, such as diffusion, or ion implantation and annealing of an n-type material which can be identical or similar to the n-type material used to create n-type region 128. As further illustrated in FIG. 5, the silicon substrate 122 is etched along its (111) plane by known etching methods, such as etching in potassium hydroxide (KOH) or the like. The back of the substrate 112 can also be etched with a teflon jig. As illustrated, the etching process etches away a central portion of silicon substrate 122 down to the silicon dioxide 124 to create an opening 132 in the silicon substrate 122.

Figure 6:
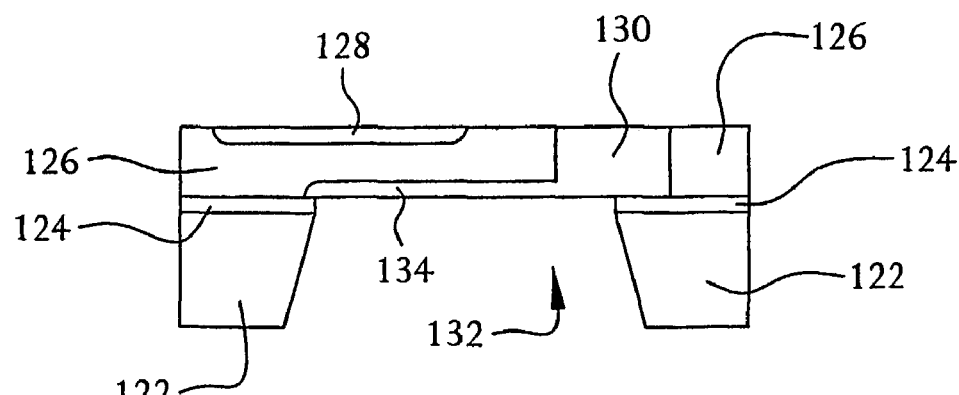
FIG. 6 illustrates a cross-sectional view of the SOI substrate shown in FIG. 5 in which a portion of the insulator has been etched away and another shallow n-type region has been formed in the silicon layer.

As shown in FIG. 6, the portion of the silicon dioxide 124 exposed in opening 132 is etched away by conventional etching methods, such as etching in hydrofluoric acid, reactive etching or the like. Another shallow n-type region 124 is created in the area of the p-type silicon 126 exposed at opening 132 by known methods, such implantation or diffusion of an n-type material identical or similar to those used to create n-type regions 128 and 130.

Figure 7:
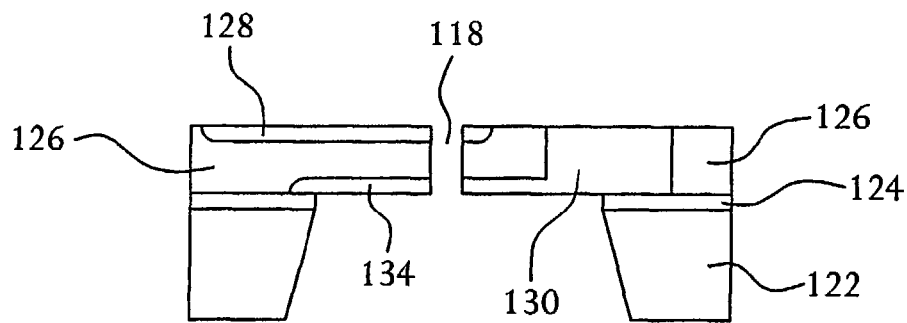
FIG. 7 illustrates a cross-sectional view of the SOI substrate having an opening etched therethrough.
Figure 8:
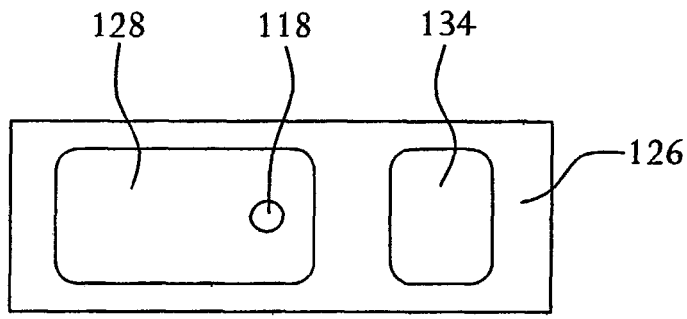
FIG. 8 illustrates a top view of the SOI substrate as shown in FIG. 7.
Figure 9:
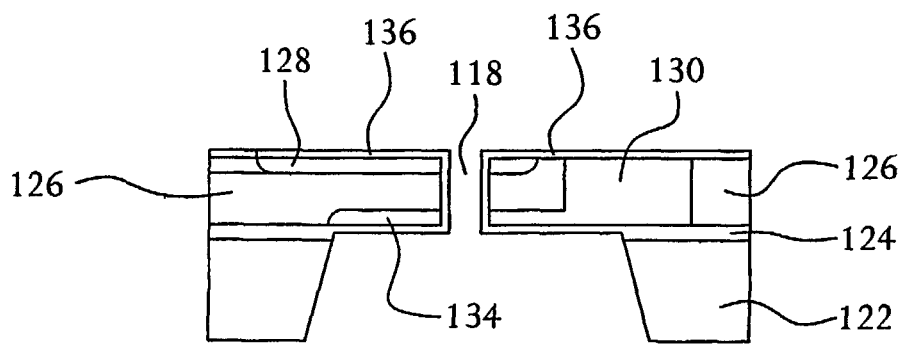
FIG. 9 illustrates a cross-sectional view of the SOI substrate shown in FIG. 7 having an oxidation layer formed on the silicon layer and on the walls forming the opening therein.
Figure 10:
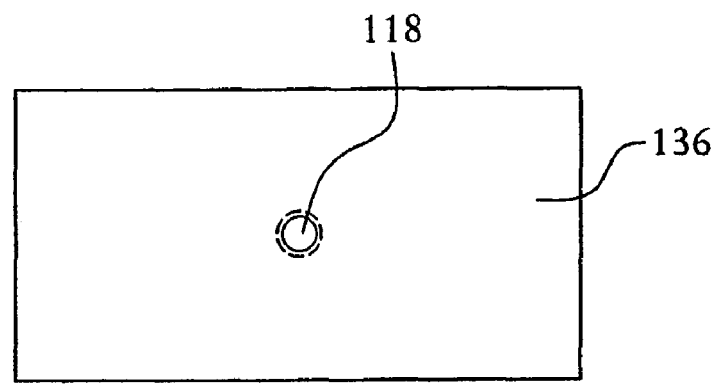
FIG. 10 illustrates a top view of the SOI substrate as shown in FIG. 9.
Figure 11:
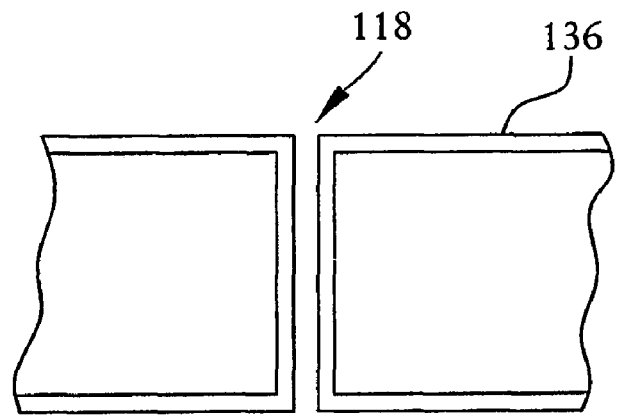
FIG. 11 illustrates a detailed cross-sectional view of the SOI substrate shown in FIG. 7 having an oxidation layer formed on the silicon layer and on the walls forming the opening therein.
Figure 12:
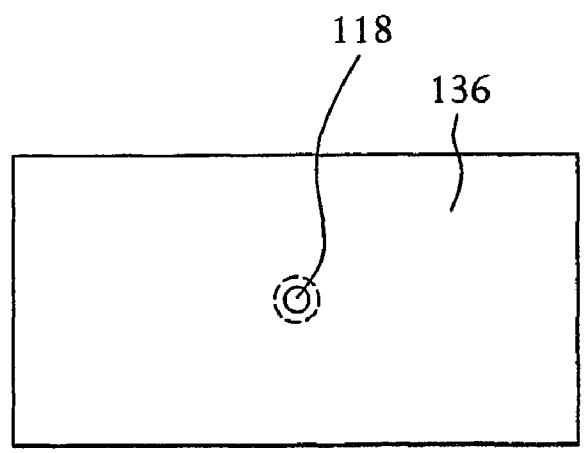
FIG. 12 illustrates a top view of the SOI substrate shown in FIG. 11.

Opening 118 (see FIGS. 1 and 2) is then formed through the n-type region 128, p-type silicon 126 and bottom n-type region 134 as shown, for example, in FIGS. 7 and 8 by reactive ion etching (RIE) using Freon 14 ($CF_4$), optical lithography, electron-beam lithography or any other fine-line lithography, which results in an opening having a diameter of about 10 nm. As shown in FIG. 9, the diameter of the opening can be further decreased by oxidizing the silicon, thus forming a silicon dioxide layer 136 over the p-type silicon layer 126 and the walls forming opening 118. This oxidation can be formed by thermal oxidation of the silicon in an oxygen atmosphere at 800–1000° C., for example. As shown in detail in FIGS. 11 and 12, the resulting oxide has a volume larger than the silicon consumed during the oxidation process, which further narrows the diameter of opening 118. It is desirable if the diameter of opening 118 can be as small as 1 nm.

Figure 13:
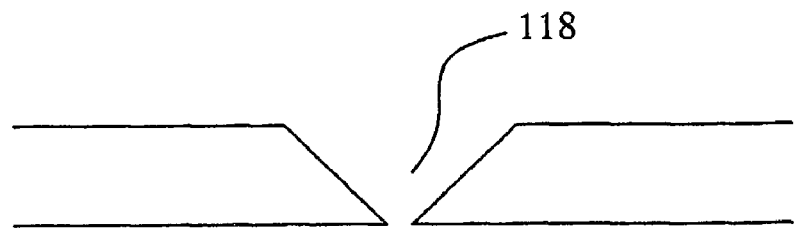
FIG. 13 illustrates a detailed cross-sectional view of an exemplary configuration of the opening in SOI substrate shown in FIG. 7.
Figure 14:
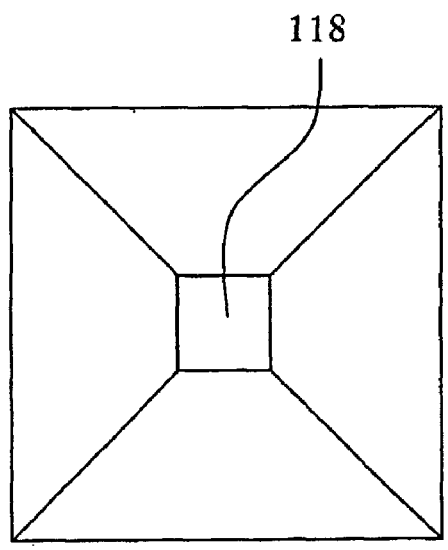
FIG. 14 illustrates a top view of the opening shown in FIG. 13.

Although for illustration purposes FIGS. 1, 2 and 3–9 show opening 118 as being a cylindrically-shaped opening, it is preferable for opening 118 to have a funnel shape as shown, for example, in FIGS. 13 and 14. This funnel-shaped opening 118 is created by performing V-groove etching of the (100) p-type silicon layer 126 using potassium hydroxide (KOH), which results in V-shaped grooves formed along the (111) planes 138 of the p-type silicon 126. The V-shaped or funnel-shaped opening, as shown explicitly in FIG. 14, facilitates movement of a DNA strand through opening 118, and minimizes the possibility that the DNA strand will become balled up upon itself and thus have difficulty passing through opening 118. Oxidation and V-groove etching can be combined to yield even smaller openings. Additionally, anodic oxidation can be used instead of thermal oxidation, as described above. Anodic oxidation has the additional advantage of allowing for monitoring of the opening size during oxidation so that the process can be stopped when the optimum opening size is achieved.

Specifically, the opening 118 should be small enough to allow only one molecule of the DNA strand 111 to pass through at onetime. Electron-Beam lithography can yield an opening 118 as small as 10 nm, but even smaller openings are needed. Oxidation of the silicon and V-groove etching as described above can be used to further reduce the opening to the desired size of 1–2 nm. Oxidation of silicon is known to yield silicon dioxide with a volume which is about twice that of the silicon consumed during the oxidation. Oxidation of a small opening 118 will result in a gradually reduced opening size, thereby providing the desired opening size V-groove etching of (100) oriented silicon using KOH results in V-grooves formed by (111) planes. KOH etching through a square $SiO_2$ or $Si_3N_4$ mask results in a funnel shaped opening with a square cross-section. Etching through the thin silicon layer results in an opening 118 on the other side, which is considerable smaller in size.

Oxidation and V-groove etching can also be combined to yield even smaller openings 118. Anodic oxidation can be used instead of thermal oxidation, which has the additional advantage of enabling the size of the opening 118 to be monitored during the oxidation and the oxidation can be stopped when the appropriate size of the opening 118 is obtained.

Figure 15:
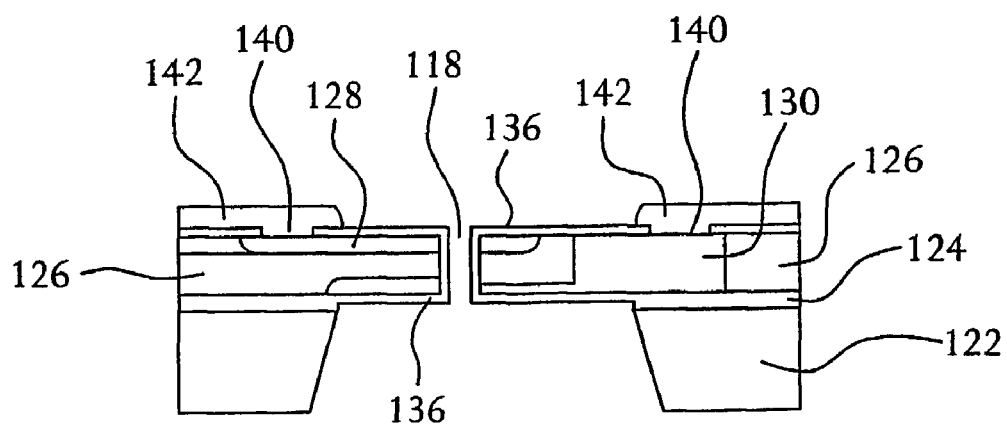
FIG. 15 illustrates a cross-sectional view of the SOI substrate as shown in FIG. 9 having holes etched in the oxidation layer and metal contacts formed over the holes to contact the shallow and deep n-type regions, respectively.
Figure 16:
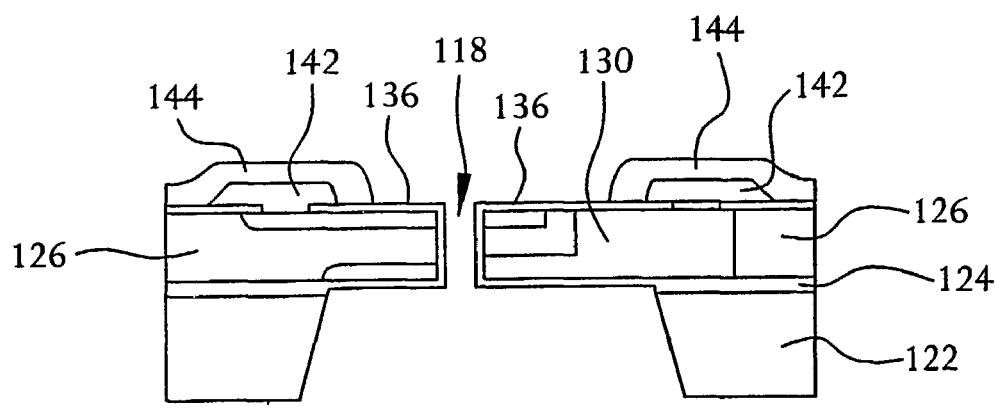
FIG. 16 illustrates a cross-sectional view of the DNA or RNA sequencer shown in FIG. 1 having been fabricated in accordance with the manufacturing steps shown in FIGS. 4–15.

Turning now to FIG. 15, holes 140 are etched into the silicon dioxide 136 to expose n-type region 128 and n-type region 130. Metal contacts 142 are then deposited onto silicon dioxide layer 136 and into holes 140 to contact the respective n-type regions 128 and 130. An insulator 144 is then deposited over metal contacts 142 as shown in FIG. 16, thus resulting in device 102 as shown in FIG. 1.

As further shown in FIG. 1, a portion of insulator 144 can be removed so that leads 116 can be connected to the n-type regions 128 and 130, which thus form the drain regions 104 and source 106, respectively. An additional insulator 146 is deposited over insulator 144 to seal the openings through which leads 116 extend to contact n-type regions 128 and 130. The completed device 102 can then be operated to perform the DNA sequencing as discussed above.

To identify the bases of the DNA molecule, it is desirable to measure a single electronic charge. If the sequencing device 102 is made to have a length and width of 0.1 by 0.1 μm, and the thickness of the silicon dioxide layer is 0.1 μm along the walls of the opening 118, a capacitance of 0.35 fF, a voltage variation of 0.45 mV, a device transconductance of 1 mS and a current variation of 0.5 nA are realized. Accordingly, a sequencing device 102 having these dimensions and characteristics can be used to detect a single electronic charge. The sequencing device 102 can further be reduced in size to obtain a sufficient special resolution to distinguish between different nucleotides. The sequencing device 102 is preferably made smaller to have an improved charge sensing capability. For example, the width of the sequencing device can be 10 nm, the length can be 10 nm, and the opening 118 can have a diameter of 1 nm.

Figure 17:
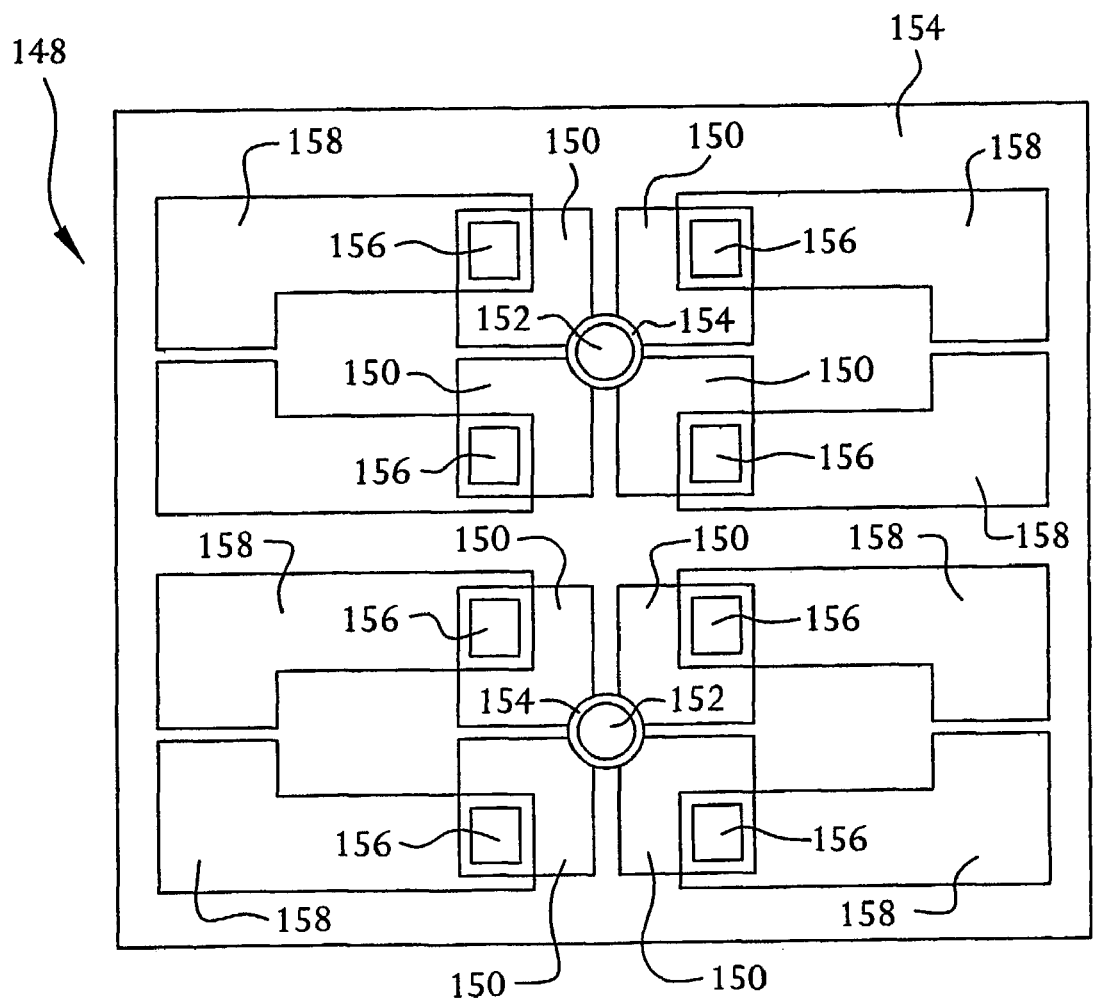
FIG. 17 illustrates a top view of a DNA or RNA sequencer having multiple detectors formed by multiple n-type regions according to another embodiment of the present invention.

Additional embodiments of the device 102 can also be fabricated. For example, FIG. 17 illustrates a top view of a nucleic acid sequencing device according to another embodiment of the present invention. In this embodiment, the steps described above with regard to FIGS. 3 through 16 are performed to form the n-type regions which ultimately form the drain and source regions. However, in this embodiment, the n-type region 128 shown, for example, in FIG. 5, is formed as four separate n-type regions, 150 in a p-type silicon layer similar to p-type silicon layer 126 described above. A silicon dioxide layer 152 covers the p-type silicon layer into which n-type regions 150 have been created.

Holes 156 are etched into silicon dioxide layer 152 so that metal contacts 158 that are deposited on silicon dioxide layer 152 can contact n-type regions 150. By detecting current flowing between the four drain regions formed by n-type regions 150 and the source region (not shown), the spatial orientation of the bases on the DNA strand passing through opening 152 can be detected.

Figure 18:
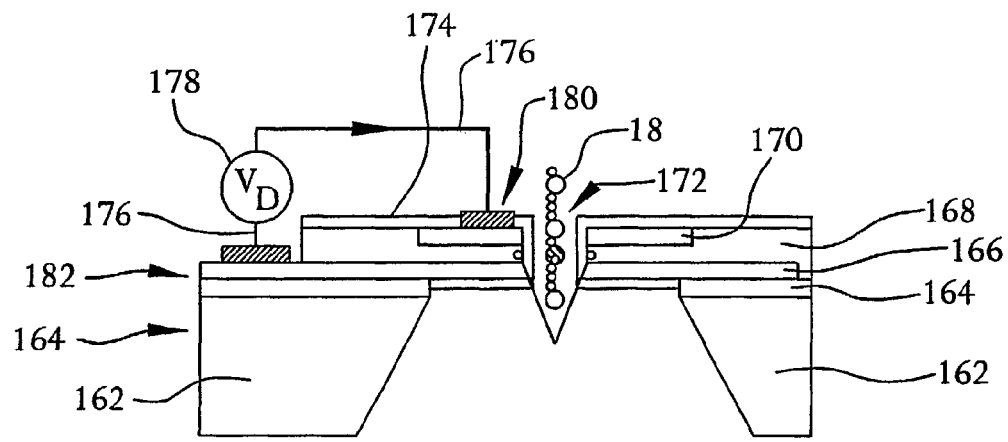
FIG. 18 illustrates a cross-sectional view of a DNA or RNA sequencer according to another embodiment of the present invention.

FIG. 18 is a cross section of a nucleic acid sequencing device 160 according to another embodiment of the present invention. Similar to nucleic acid sequencing device 102, 160 includes a silicon substrate 162, a silicon dioxide layer 164, an n-type region 166 implanted in p-type silicon 168, and a second n-type region 170 implanted in p-type silicon 168. Nucleic acid sequencing device 160 further has an opening 172 passing therethrough. The opening can be cylindrical, or can be a V-shaped or funnel-shaped opening as described above. A silicon dioxide layer 174 covers p-type silicon layer 168, n-type region 170 and n-type region 166 as shown, and decreases the diameter of opening 172 in the manner described above. An opening is etched into silicon dioxide layer 172 to allow a lead 176 to be attached to n-type region 170. Another lead 176 is also attached to an exposed portion of n-type region 166, so that a voltage source 178 can apply a potential across the drain region 180 formed by n-type region 170 and source region 182 formed n-type region 166. The nucleic acid sequencing device 160 can thus be used to detect the bases of a DNA strand 182 in a manner described above.

Figure 19:
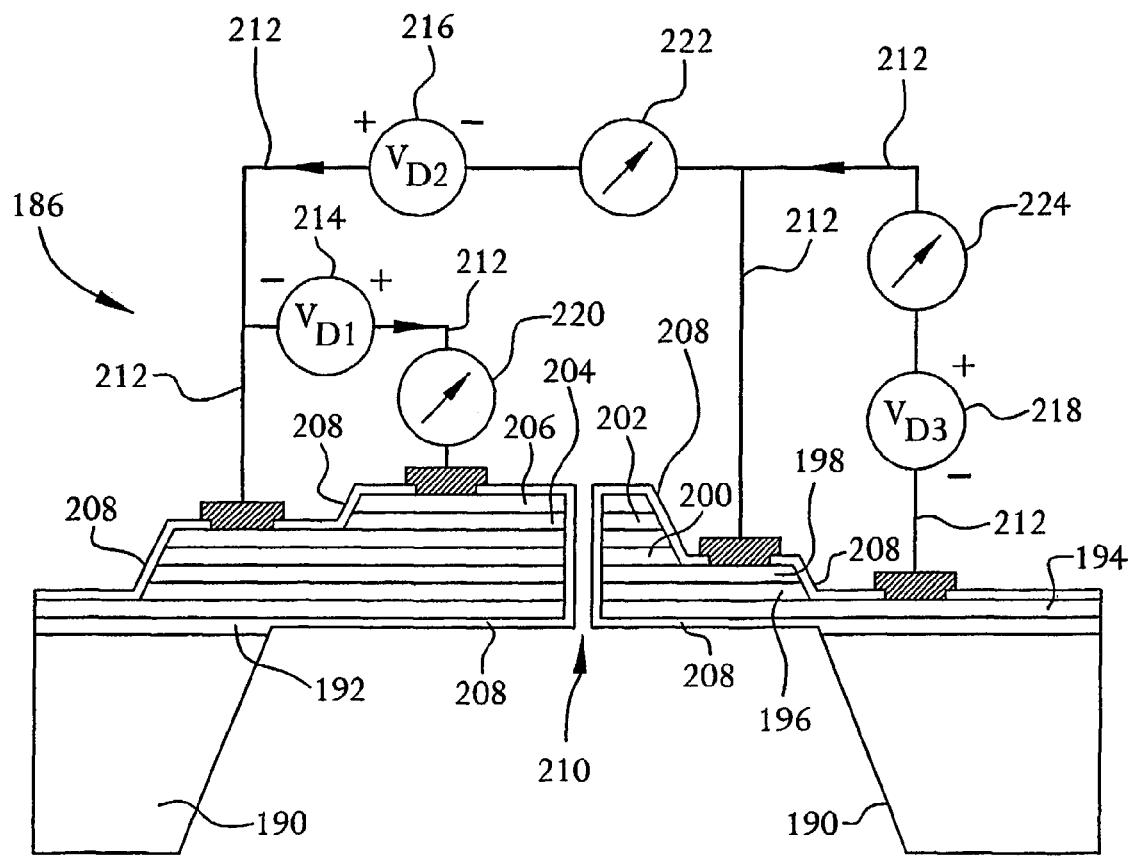
FIG. 19 illustrates a cross-sectional view of a DNA or RNA sequencer according to a further embodiment of the present invention.

FIG. 19 illustrates a DNA sequencing system 186 according to another embodiment of the present invention. System 186 includes a multi-layer nucleic acid sequencing device 188 which, in this example, comprises three MOSFET-type devices stacked on top of each other. That is, device 188 includes a silicon substrate 190 similar to silicon substrate 122 described above. A silicon dioxide layer 192 is present on silicon substrate 190. The device 188 further includes an n-type doped silicon region 194, a p-type silicon dioxide region 196, an n-type doped silicon region 198, a p-type silicon dioxide region 200, an n-type doped region silicon region 202, a p-type silicon dioxide region 204 and an n-type doped silicon region 206. Regions 194 through 206 are stacked on top of each other as shown explicitly in FIG. 19. However, as can be appreciated by one skilled in the art, the polarity of the layers can be reversed for this embodiment, and for any of the other embodiments discussed herein. That is, the device 188 can comprise a p-type doped silicon region 194, an n-type silicon dioxide region 196, a p-type doped silicon region 198, and so on.

Additionally, a thin silicon dioxide layer 208 is formed over the layers as illustrated, and is also formed on the walls forming opening 210 to decrease the diameter of opening 210 in a manner described above with regard to opening 118. Also, opening 210 can be cylindrically shaped, a V-shaped groove or a funnel-shaped groove as described above. Holes are formed in silicon dioxide layer 208 so that leads 212 can be attached to regions 194, 198, 202 and 206 to couple voltage source 214, 216 and 218 and current meters 220, 222 and 224 to device 188 as will now be described. Voltage sources 214, 216 and 218 and current meters 220, 222 and 224 are similar to voltage source 112 and current meter 114, respectively, as described above.

Specifically, leads 212 couple voltage source 214 and current meter 220 in series to n-type doped silicon region 202 and n-type doped silicon region 206. Therefore, voltage source 214 applies a voltage across regions 202 and 206 which are separated by p-type silicon dioxide region 204. Leads 212 also couple voltage source 216 and current meter 222 to n-type doped silicon region 198 and n-type doped silicon region 202 as shown. Furthermore, leads 212 couple voltage source 218 and current meter 224 to n-type doped silicon region 194 and n-type doped silicon region 202 as shown. Accordingly, as can be appreciated from FIG. 19, n-type doped silicon region 198 and n-type doped silicon region 194 act as the drain and source regions, respectively, of one MOSFET, n-type doped silicon region 202 and n-type doped silicon region 198 act as drain and source regions, respectively, of a second MOSFET, and n-type doped silicon region 206 and n-type doped silicon region 202 act as drain and source regions, respectively, of a third MOSFET. These three MOSFET type devices can measure the current induced by the bases of a DNA strand passing through opening 210, and thus take multiple measurements of these bases to improve accuracy.

Figure 20:
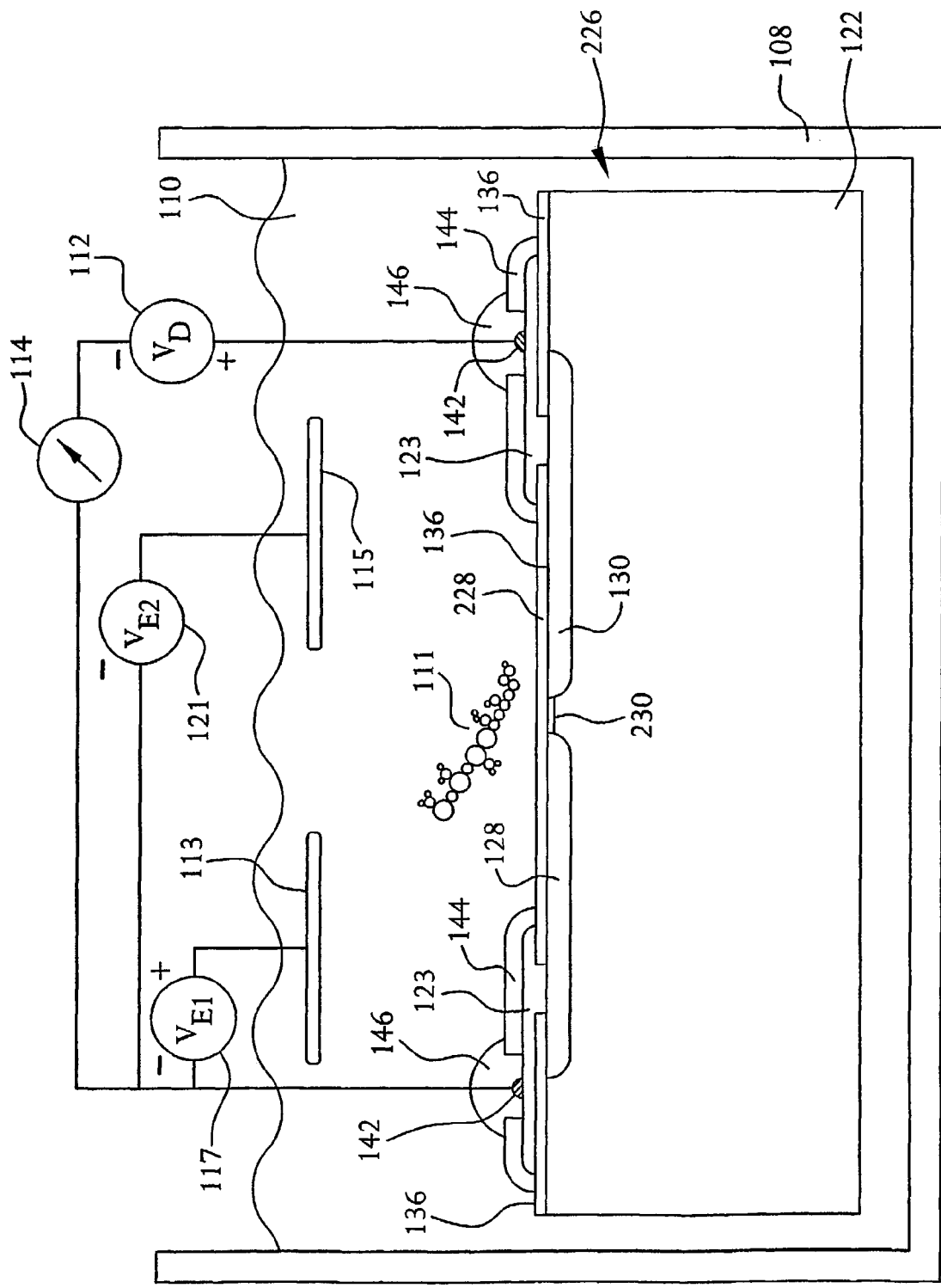
FIG. 20 illustrates a cross-sectional view of a DNA or RNA sequencer according to a further embodiment of the present invention.
Figure 21:
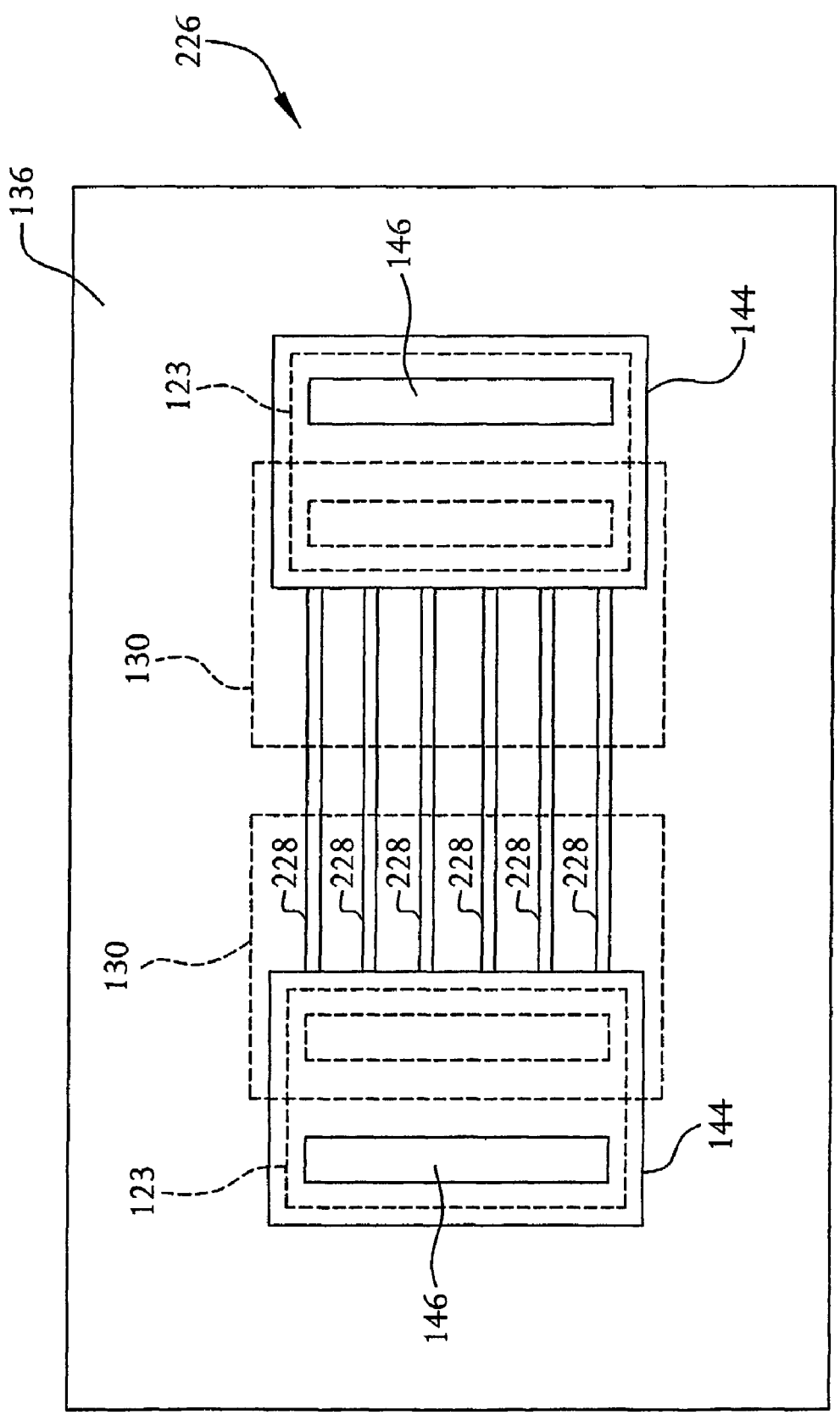
FIG. 21 illustrates a top view of the DNA or RNA sequencer shown in FIG. 20.

It is also noted that a nucleic acid sequencing device above can be configured to sense the bases of a nucleic acid strand without it being necessary for the DNA strand to pass through an opening in the devices, as shown in FIGS. 20 and 21. That is, using the techniques described above, a nucleic acid sequencing device 226, similar to nucleic acid sequencing device 102 shown in FIG. 1, can be fabricated having its drain and source regions proximate to a surface. It is noted that like components shown in FIGS. 1, 20 and 21 are identified with like reference numbers. However, in place of an opening 118, one or more grooves 228 can optionally be formed in the surface extending from the drain region to the source region. Alternatively, no grooves are formed in the surface, but rather, the detection area for detecting nucleic acid strands 111 is present between the drain and source regions. Techniques similar to those discussed above, such as the application of voltage potentials, by means of voltage sources 117 and 121, and creation of a pressure differential in the container 108 can be used to move the nucleic acid strands 111 in a horizontal direction along the surface of the device over the grooves 228. The bases in the nucleic acid strands create an image charge channel 230 between the drain and source regions which allows current to flow between the drain and source regions. The current induced in the nucleic acid sequencing device by the bases can be measured in a manner similar to that described above.

Again, it is noted that the device 226 differs from the other embodiments represented in FIGS. 1, 17 and 19 in that the channel 230 containing the image charge is horizontal rather than vertical. The structure no longer contains an opening 118 as in the device 102 shown in FIGS. 1, 17 and 19, but rather this embodiment contains a charge sensitive region just above channel 230. Similar to FIG. 1, the external electrodes 113 and 115 are used to apply an electric field which steers the nucleic acid strands 111 towards or away from the charge sensitive region. That is, the motion of the nucleic acid strands 111 is controlled by applying a voltage to the external electrodes 113 and 115 relative to the voltage applied to the doped regions 130. Additional electrodes (not shown) can be added to move the nucleic acid strands 111 perpendicular to the plane shown in FIG. 20.

The charge sensitive region of the device is located just above the channel 230 and between the two doped regions 130. Identification of individual bases requires that the distance between the two doped regions is on the order of a single base and that the motion of the nucleic acid strand 111 is such that each base is successively placed above the charge sensitive region. This horizontal configuration enables more parallel as well as sequential analysis of the nucleic acid strands 111 and does not require the fabrication of a small opening. Additional surface processing, such as the formation of grooves 228 as discussed above that channel the nucleic acid strands 111 can be used to further enhance this approach.

The horizontal embodiment shown in FIGS. 19 and 20 is also of interest to detect the presence of a large number of nucleic acid strands 111. For instance, using an electrophoresis gel as the medium, one starts by placing nucleic acid strands 111 of different length between the electrodes 113 and 115. A negative voltage is applied to the electrodes 113 and 115, relative to the doped regions 130. The nucleic acid strands 111 will then move towards the charge sensitive region. The smaller strands will move faster and the larger strands will move slower. The smaller strands will therefore arrive first at the charge sensitive region, followed by the larger ones. The charge accumulated in the charge sensitive region and therefore also the image charge in the channel 230 therefore increases "staircase-like" with time. This results in a staircase-like increase or decrease of the current measured by current meter 114.

While this operation does not yield the identification of the individual bases of a single DNA/RNA strand, it does provide a measurement of the length of the strands equivalent to the one obtained by an electrophoresis measurement. The advantage over standard electrophoresis is that a real-time measurement of the position of the DNA/RNA strands is obtained. In addition, the dimensions can be reduced dramatically since micron-sized devices can readily be made, while standard electrophoresis uses mm if not cm-sized drift regions. This size reduction leads to faster measurements requiring less DNA/RNA strands, while also reducing the cost of a single charge sensing device.

Figure 22:
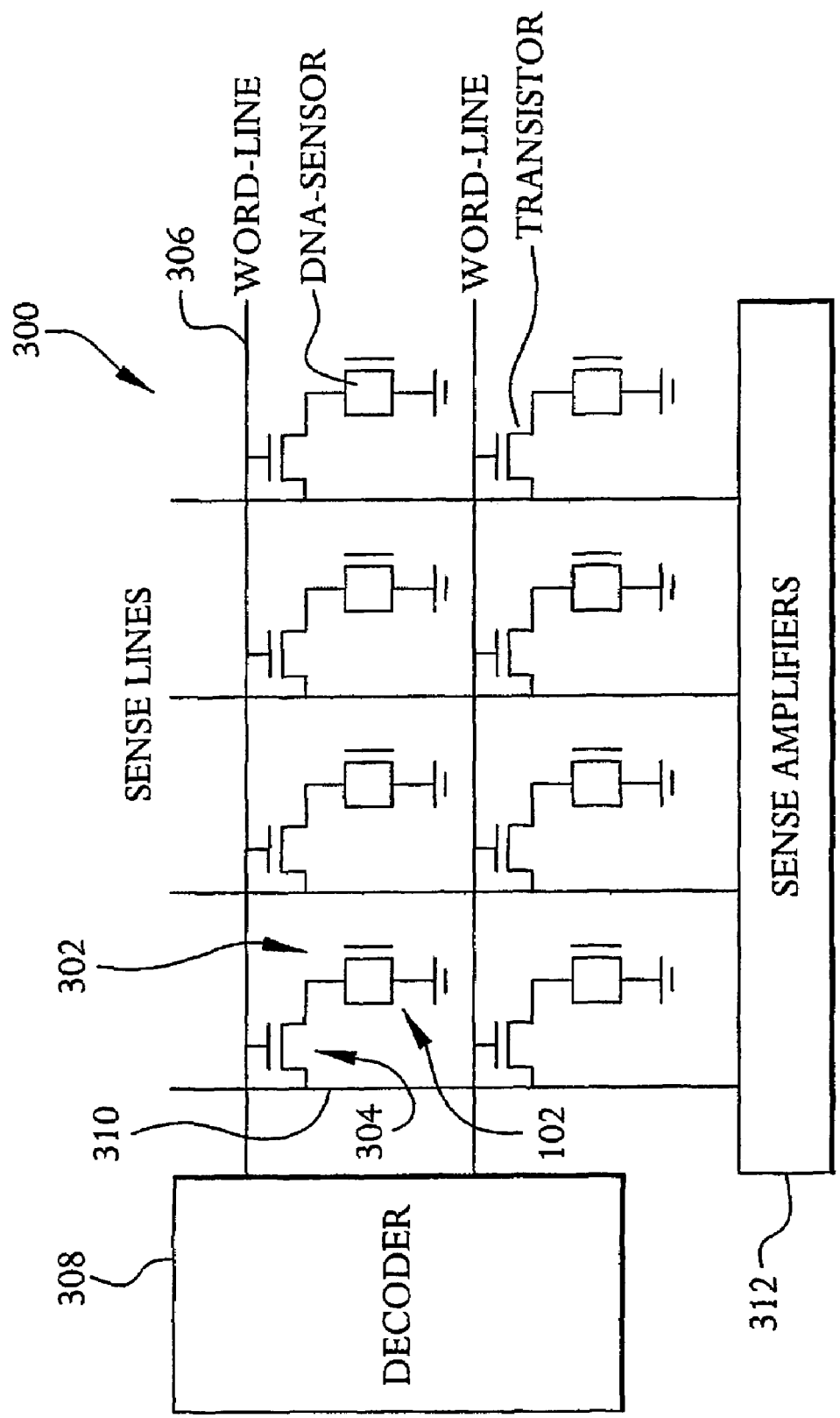
FIG. 22 is a conceptual block diagram illustrating an example of a matrix arrangement of DNA or RNA sequencers.

It is further noted that multiple DNA sensors (e.g., sequencing devices 102) can be organized into a two-dimensional array 300 with electronic addressing and read-out as shown in FIG. 22. The array consists of cells 302, which contain the sequencing devices 102 connected on one side to ground and on the other side connected to the source, for example, of a transistor 304, so that the drain-source current of a sequencing device 102 will flow into the source of its corresponding transistor 304. The gates of the transistors 304 are connected to the word lines 306, which in turn are connected to a decoder 308. The drain of the transistor 304 in each cell 302 is connected to a sense line 310. The sense lines 310 are connected to a series of sense amplifiers, shown as sense amplifier 312.

The array 300 is operated by supplying an address to the decoder 308 from a controller, such as a microprocessor or the like (not shown). The decoder 308 then applies a voltage to the word-line 306 corresponding to the address. The sense amplifiers 312 provide the bias voltage to the selected row of sequencing devices 102. The bias voltage causes the flow of DNA molecules through the opening 118 in the selected sequencing device. The selected sequencing device 102 provides to its corresponding transistor 304 a current which is proportional to the charge of the individual nucleotides in the manner described above. The sense amplifiers measure the current of each sequencing device 102 that is selected. The array 300 thus enables multiple simultaneous measurements, which increasing the sequencing rate as compared to as single sequencing device 102 and also providing redundancy and additional tolerance to defective sequencing devices 102.

In addition, any of the DNA sequencers described above (e.g., sequencing device 102) can contain an alternative to the barrier (e.g., oxide layer 136) between the semiconductor channel (e.g., channel 119 in sequencing device 102 shown in FIG. 1) and the medium containing the DNA molecules (e.g., liquid 110 shown in FIG. 1). For example, the oxide barrier 136 can be removed, which still leaves a potential barrier between the semiconductor and the medium. The oxide layer 136 can be replaced by a wider bandgap semiconductor doped with donors and/or acceptors. The oxide layer 136 can also be replaced by an undoped wider bandgap semiconductor layer.

Furthermore, the oxide layer 136 can be replaced with an oxide containing one or more silicon nanocrystals. The operation of a sequencing device 102 with this type of a barrier is somewhat different compared than that of a sequencing device 102 with an oxide layer 136. That is, rather than directly creating an image charge in the semiconductor channel 119, the charge of the individual nucleotides polarizes the nanocrystal in the barrier. This polarization of the nanocrystal creates an image charge in the semiconductor channel 119. The sensitivity of the sequencing device 102 will be further enhanced as electrons tunnel from the nucleotide into the nanocrystal. The charge accumulated in the nanocrystal can be removed after the measurement (e.g., current reading by current meter 114) by applying a short voltage pulse across the drain and source of the sequencing device 102.

Any of the sequencing devices described above (e.g., sequencing device 102) can also be constructed without the use of a semiconductor. In this arrangement, the middle p-type semiconductor 126 (see FIG. 1) is replaced with an insulating layer such as silicon dioxide, while the n-type source region 106 and drain region 104 are replaced by metal electrodes. The oxide layer between the two metal electrodes must be thin enough (less than 10 nm) so that electrons can tunnel through the oxide layer. The oxide separating the two metal electrodes can be made thinner around the opening, so that tunneling only occurs at the opening.

Figure 23:
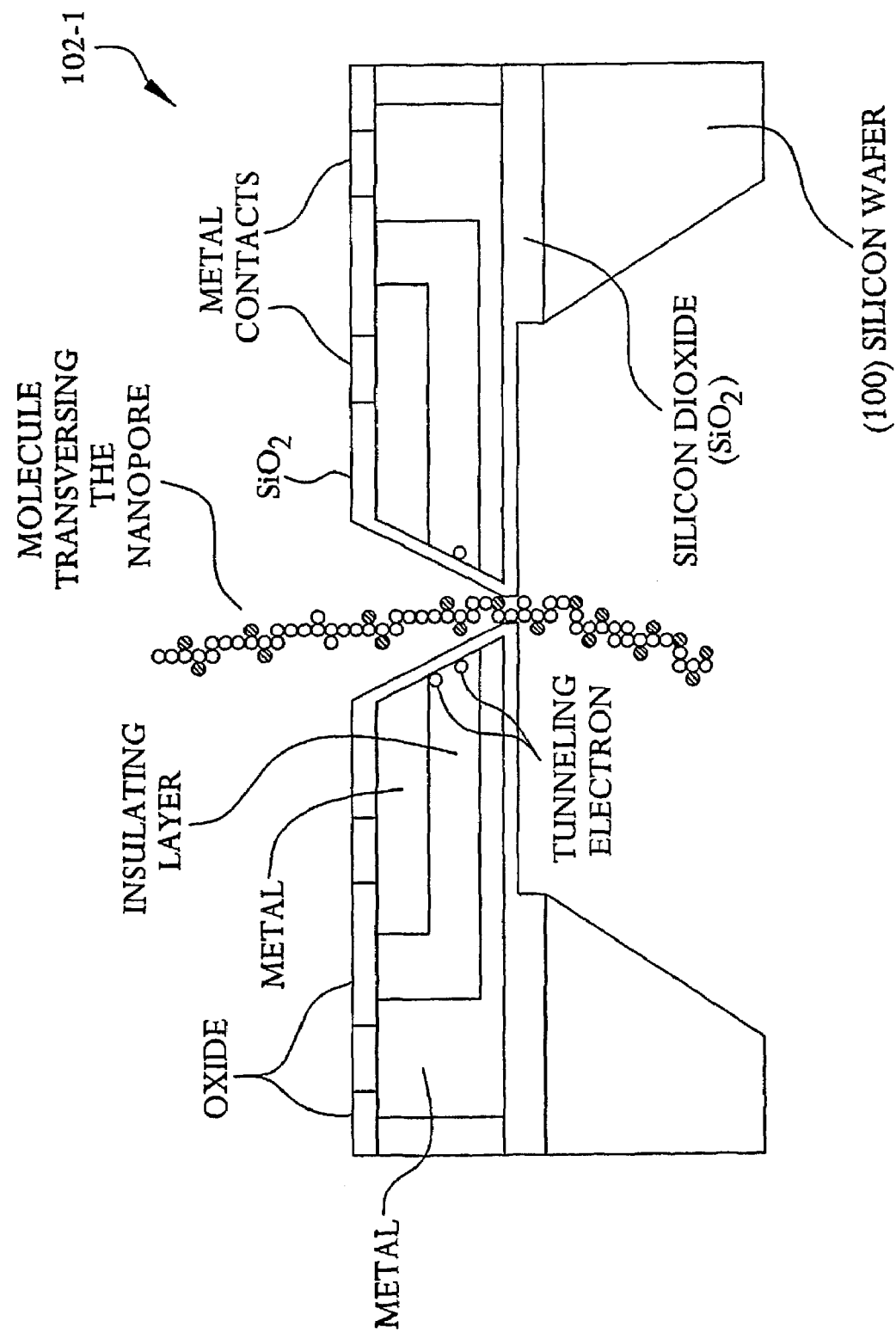
FIG. 23 is a cross-sectional view of a sequencer having a metal layer in place of a middle semiconductor layer to achieve electron tunneling.

The operation of this type of sequencing device 102-1 is described as follows with reference to FIG. 23. As a DNA molecules passes by the thin oxide layer, it changes the local potential in the oxide and causes a current variation due to tunneling of electrons through the oxide layer. Since the barrier separating the molecules from the channel 119 is very thin, tunneling of electrons can occur to and from the molecules. This tunneling can take place to/from the molecule from/to the channel 119. This current is expected to be much smaller than the current in the channel 119 because of the large amplification within the sequencing device. However tunneling to and from the nanocrystal (as described above as an alternate barrier material) will provide a similar amplification. This tunneling will therefore provide useful and measurable information about the charge distribution along the DNA molecule.

As discussed above, the size of the opening in the sequencing device (e.g., opening 118 in sequencing device 102) can be varied over a large range. However for proper operation, the opening 118 must be small enough so that the DNA is in close proximity to the charge sensor and large enough so that the DNA can traverse the opening. Since the diameter of a single stranded DNA molecule equals about 1.5 nm, the opening should be between 1 and 3 nm for optimal sensing. Larger openings may result in reduced signal to noise ratio, but would provide a larger ion flow through the opening 118.

Figure 24:
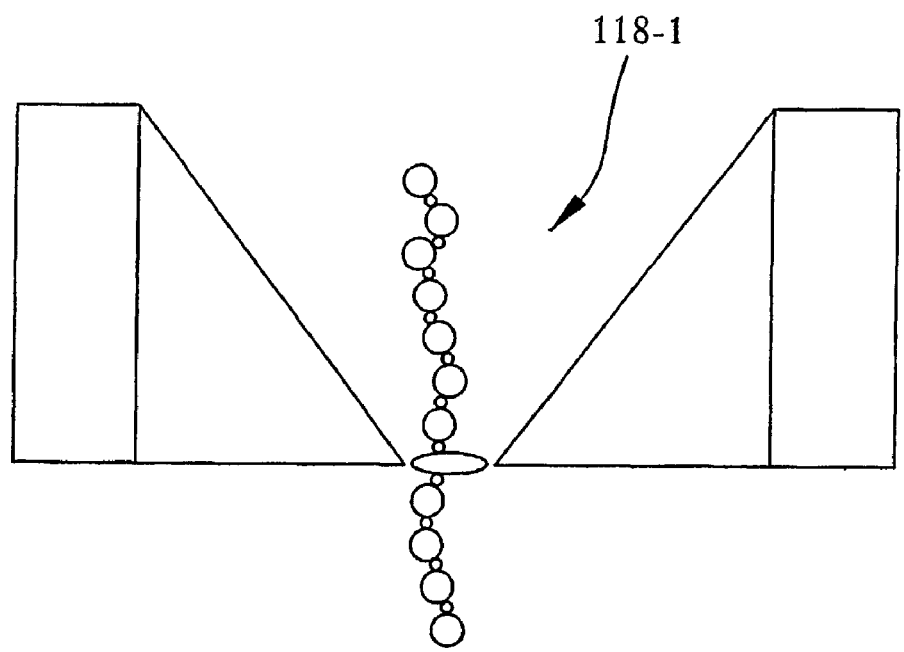
FIG. 24 illustrates a detailed cross-sectional view of another exemplary configuration of the opening in SOI substrate shown in FIG. 7.
Figure 25:
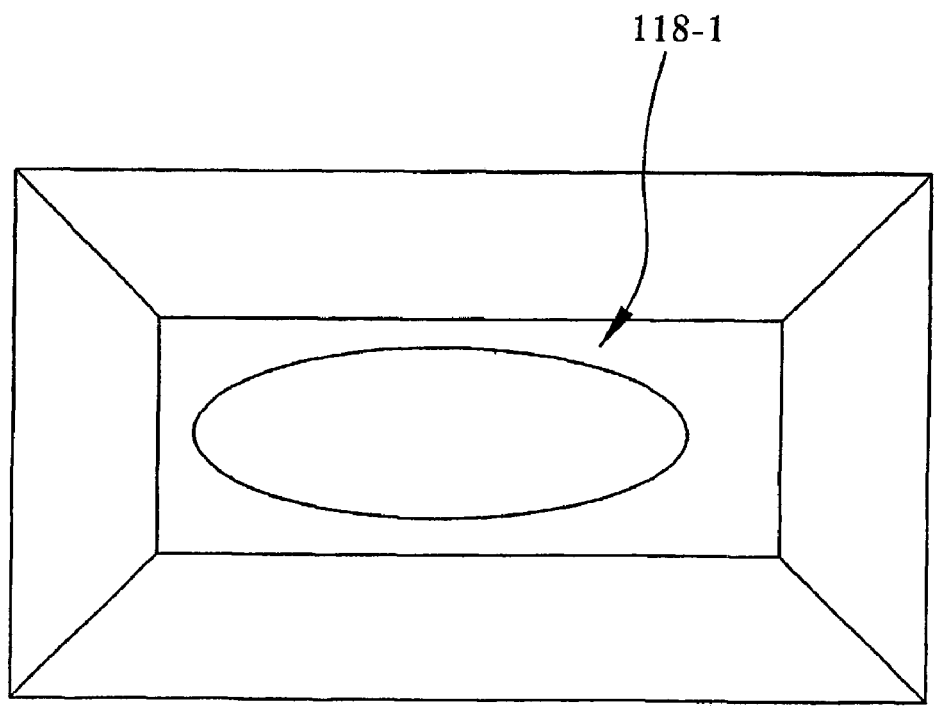
FIG. 25 illustrates a top view of the opening shown in FIG. 24.

It is further noted that certain advantages can be achieved by making the opening in the sequencing device asymmetric. For example, as shown in FIGS. 24 and 25, which correspond to FIGS. 13 and 14 as their related discussion above, by making the initial pattern before V-groove etching asymmetric, the final opening 118 will also be asymmetric, for example, an oval or a rectangle. Then the nucleotides, which are asymmetric, will have a preferred orientation as they pass through the opening 118. This removes the ambiguity in identifying the properties of the nucleotides due to their rotation around their backbone axis, and greatly simplifies analysis of the sensor signals. In addition, an electric field could be imposed along the longer axis of the opening 118 to align the base intrinsic dipole moment of the nucleotide with the field. For example, the dipole moment of Cytosine is 6.44 Debye, the dipole moment of Thymine is 4.50 Debye, the dipole moment of Adenine is 2.66 Debye and the dipole moment of Guanine is 6.88 Debye. If the field is strong enough, it can stretch the base (nucleotide) along the dipole moment, thus bringing the charges on the base nearer to the sensors increasing sensitivity. These techniques will thus make the data much easier to interpret, and will increase the signal used to discriminate between bases.

Figure 26:
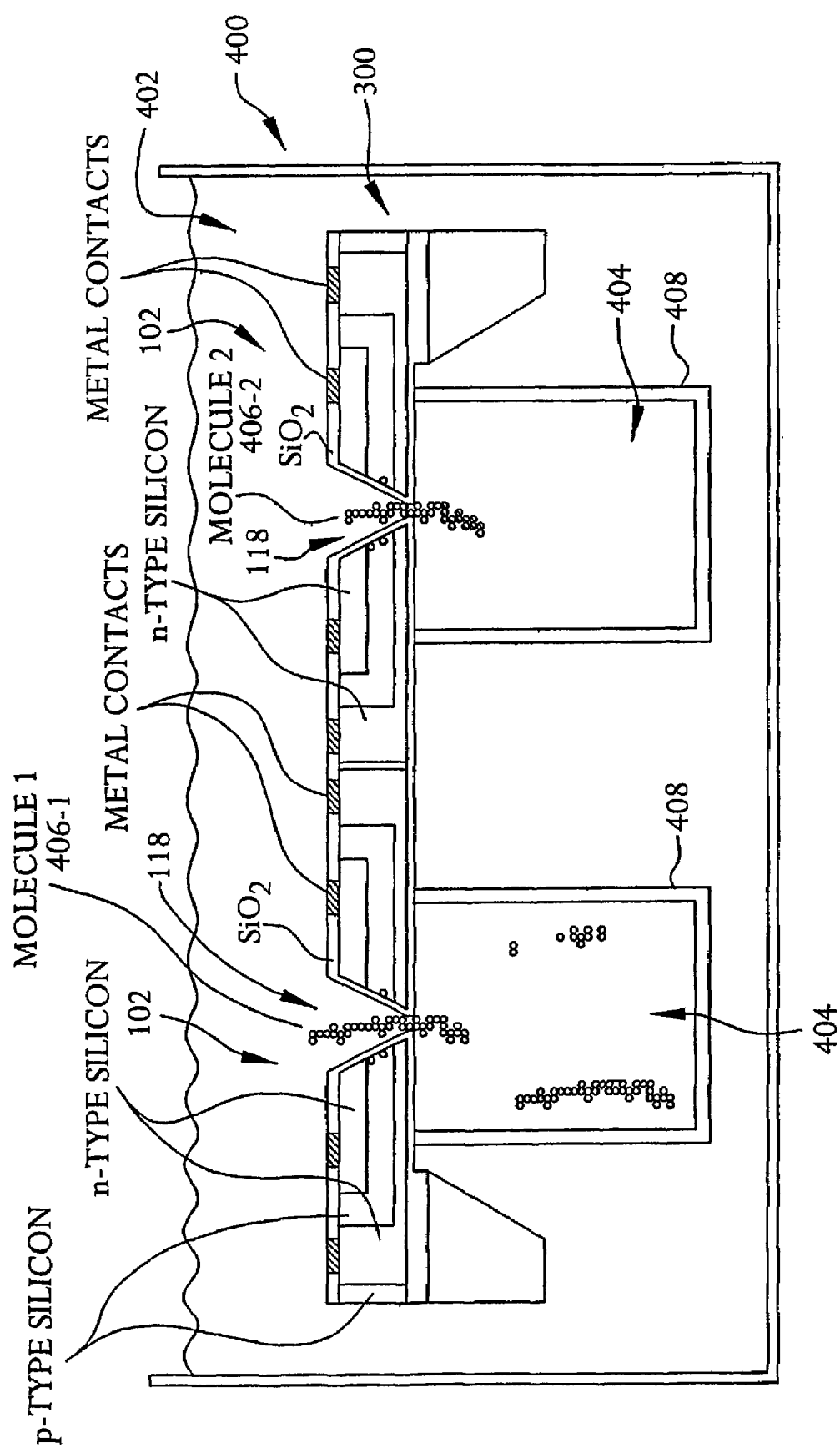
FIG. 26 illustrates a cross-sectional view of a multi-opening sequencer used with separate liquid regions.

In addition, as shown in FIG. 26, array 300 of the sequencing devices described above (e.g. sequencing device 102) can be used in an arrangement in which the liquid in a vessel 400 is divided into two regions, namely, a source region 402 and one or more collection regions 404. The source region 402 contains ions, fluid such as water, gel or the other types of liquids described above, and several kinds of nucleic acid strands 406-1 and 406-2, such as DNA strands.

As shown, a collection region 404 can be formed by a collection vessel 408. The collection vessel 408 can isolate the liquid in collection region 404 from the fluid in source region 402, in which case the fluid in source region 402 can be the same as or different than the fluid in collection region 404. Alternatively, the collection vessel 408 can be porous to allow the fluid in collection region 404 to flow into source region 402 and vice-versa while being impermeable to the nucleic acid strands 406-1 and 406-2, thus prohibiting the nucleic acid strands 406-1 and 406-2 from passing through the collection vessel 408 from the source region 402 into the collection region 404 and vice-versa.

The source region might contain many extraneous DNA strands plus many strands of a particular type of DNA (type X) with a known or partially known-nominal sequence. Then the array 300 can be controlled as described above to draw DNA strands through the openings (e.g., openings 118) in the N sequencing devices 102 operating in the array 300, where N is a number much greater than 1 (e.g., 100 or more). As DNA strands traverse the openings 118 and are sequenced, the extraneous strands are backed out into the source region, which is manipulated so that this strand is removed from the vicinity of the opening 118 it just exited and has a negligible chance of entering another opening.

For example, strands of type X with the nominal sequence are counted, but also rejected and sent back into the source region. However, strands of type X with one or a few differences in the base sequence detected by nano-opening j (j=1 to N) are made to traverse the openings 118 and are captured in a container containing a collection region of the fluid. Any subsequent strands of type X identical to the first strand so captured are also counted and sent to an appropriate collection container. A different (or accidentally the same) non-nominal sequence of an X strand is collected at each opening 118. When sequencing stops, the ratio of each type of non-nominal X strand to the nominal X strands is know, and a 100% pure sample of each variant type has been collected in the individual collection vessels 408. These pure samples then can be duplicated by PCR and studied individually. This process can be used, for example, in studying mutation and/or incorrect duplication rates, and therefore aging, in DNA from an individual.

All of the devices described above can also be modified in other ways. For example, the $SiO_2$ oxide layer can be converted to $Si_3N_4$ in a nitrous oxide (NO) ambient for use in alkaline solutions. Furthermore, since DNA molecules 111 are negatively charged, the molecules 111 can be attracted to the opening 118 by using electrodes, such as electrodes 113 and 115, to apply a positive voltage to the liquid 110 relative to the source of the device.

As discussed above, a gel can be used in place of liquid 110 to contain the DNA molecules. The use of a gel will slow down the motion of the ions and further improve the signal to noise ratio. Furthermore, a pressure differential can be applied across the opening to control the flow independent from the applied voltage between source and drain.

Double stranded DNA can be analyzed as well. Even though double stranded DNA is a neutral molecule, since the molecule contains charge, the nucleotides can be identified by charge sensing. In addition, other molecules, for example, a fluorescent dye such as Hoechst dye, can be attached to single stranded DNA to enhance/modify the stiffness of the molecule thereby facilitating the insertion of the molecule into the nanometer-sized opening. Furthermore, since the above devices can by used to analyze generally any types of individual polymers, they can be used in industries dealing with polymers such as the petroleum industry, pharmaceutical industry and synthetic fiber industry, to name a few.

In addition, to facilitate the measurement of the charge of a single molecule (e.g., a nucleic acid strand 111 as shown in FIG. 1), a larger size particle can be attached to a single molecule. For example, a gold nanoparticle can be attached to single-stranded DNA 6. The purpose of the gold nanoparticle is to provide a solid anchor to the DNA molecule. The gold particle can easily be charged and discharged. As a result, the gold particle and the attached DNA molecule can be manipulated by applying electric fields.

The gold nanoparticle attached to single stranded DNA will then be placed in an insulating liquid such as synthetic oil, which can be used as the liquid 110 in the arrangement shown in FIG. 1, for example. The purpose of the liquid is to allow the particle together with the DNA strand to move freely. The liquid should be insulating to avoid charge shielding by ions, which are present in conducting liquids. Synthetic oils have been identified as good candidates since they are highly resistive and do not form chemical bonds with single stranded DNA.

The charge of the gold nanoparticles can then be measured using a semiconductor-based charge sensor, such as device 102 shown in FIG. 1 that includes a floating gate, or device 226 without a gate electrode as shown in FIG. 21. As charged particles approach the device, image charges are formed at the silicon/oxide interface in the manner described above. An appropriate bias will be applied to the device (e.g., device 102) so that it operates in the sub threshold regime, where it is most sensitive to any image charge. The induced image charge then results in an increased conductivity of the device and is read out in the form of an increased current. As an example, it can be easily calculated that 100 DNA molecules, which each contain 100 bases that each carry about one third of an electronic charge, shift the threshold voltage of a 1 $\mu$m by 1 $\mu$m MOSFET with a 10 nm thick oxide by 150 mV. This shift can be measured by measuring the change in drain current of the device (e.g., as can be measured by current meter 114 shown in FIG. 1). The measured charge is expected to be affected by the presence or absence of charge-shielding cations and stray ions in DNA's hydrogen shell. Also, electric fields can be used to separate the small ions from the larger DNA molecules.

Figure 27A:
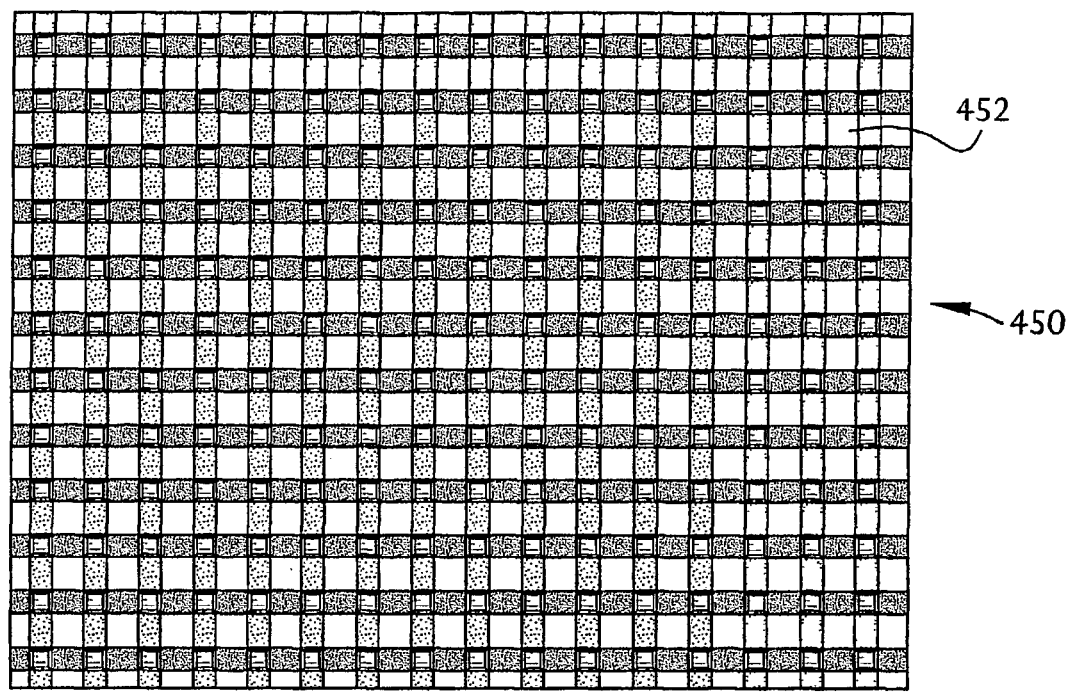
FIGS. 27A and 27B are images of photographs of opening patterns formed in a semiconductor structure.
Figure 27B:
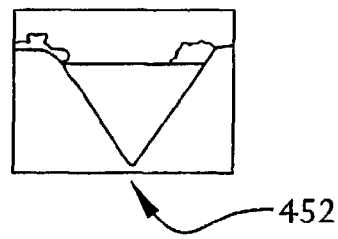

It is further noted that the types of nanometer-size openings described above, for example, opening 118 in device 102 shown in FIG. 1, can be made as well-defined square holes as shown in FIGS. 27A and 27B. To form these holes, a series of lines with the appropriate width and spacing is defined in a pattern, and the pattern is then transferred into a masking material such as $SiO_2$. The same line pattern rotated by 90° is then defined and transferred into the underlying masking material so that only the area defined by the overlapping areas between the two sets of lines is removed during etching. This process leads to a much better edge definition of the holes compared to defining the holes in a single lithographic step, as can be appreciated from the pattern 450 shown in FIG. 27A having openings 452. The pattern shown in FIGS. 27A and 27B was made with the technique described above using a line pattern with 3 $\mu$m width and 3 $\mu$m spacing. The resulting etch mask was then used to etch the pits in the silicon using potassium hydroxide (KOH).

Figures 28A, 28B:
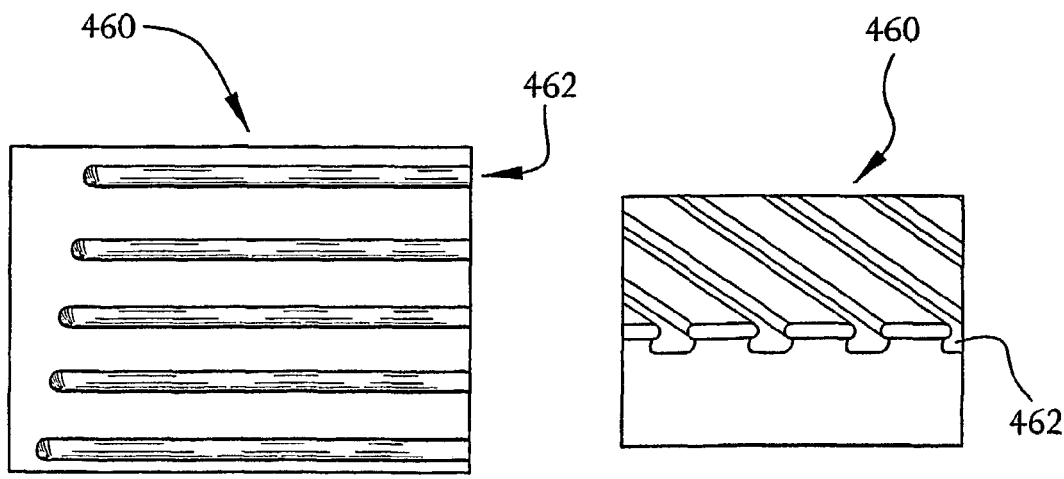
FIGS. 28A and 28B are images of photographs of opening patterns forms in a semiconductor structure.

A further reduction of the line width can be achieved using electron-beam lithography. For example, electron-beam lithography using a Phillips 515 scanning electron microscope (SEM) can produce a line pattern with a 100 nm width. Polymethyl methacrylite (PMMA) can be used as an electron resist and developed with methyl iso butyl ketone/isopropyl alcohol (MIBK/IPA) to achieve the pattern 460 shown in FIGS. 28A and 28B having openings 462. As illustrated, the lines are well defined and are limited by the spot size of the beam used in the electron-beam lithography. The beginning of each line is rounded since a single exposure with a gaussian beam has been used. This rounding can be eliminated by using the crossed-line lithography technique described with regard to FIGS. 27A and 27B. The PMMA can also be used as an etch mask to successfully transfer the pattern into a thin $SiO_2$ layer as shown.

Accordingly, an opening 118 can be fabricated on (100) silicon membranes by combining state-of-the-art electron beam lithography with two well-known size reduction techniques discussed above. A scanning transmission electron microscope (STEM) can be used to define 10 nm lines in PMMA. Crossed lines will be used to create 10 nm square holes in a $SiO_2$ mask. KOH etching can be used to etch V-shaped pits, providing a 2–4 nm opening on the other side of the silicon membrane. The opening will be further reduced in size by thermal oxidation of the silicon as it results in an oxide, which has about twice the volume of the oxidized silicon. This oxidation also provides the gate oxide, as discussed above.

Although only several exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A system for detecting at least one polymer, comprising:
at least one semiconductor device having at least one detecting region having an opening through which said polymer can pass, said opening having a cross-sectional dimension of less, than about 100 nm and being configured such that while said at least one polymer passes through said opening, a charge of at least a component of said polymer creates image charges in said region, said image charges being sufficient to increase the conductivity of said region by an amount related to said charge of said component;
said detecting region including a region of said semiconductor device including an insulating layer defining an opening in said semiconductor device having a cross-section sufficient to enable said polymer to enter said opening, such that said detecting region is adapted to detect said charge of said component in said opening, wherein said region of said detecting region includes an oxide layer defining said opening, said oxide layer including at least one silicon nanocrystal.

2. A system as claimed in claim 1, wherein: said opening is non-circular.

3. A system for detecting at least one polymer, comprising:
a plurality of semiconductor detecting devices, each having at least one detecting region having an opening through which said polymer can pass, said opening having a cross-sectional dimension of less than about 100 nm and being configured such that while said at least one polymer passes through said opening, a charge of at least a component of said polymer creates image charges in said region, said image charges being sufficient to increase the conductivity of said region by an amount related to said charge of said component, such that said detecting region is adapted to detect said charge of said component in said opening, wherein said detecting region includes an oxide layer defining said opening, said oxide layer including at least one silicon nanocrystal; and
a reader, adapted to selectably obtain a respective reading from each of said semiconductor detecting devices, said respective readings representing respective charges detected by said semiconductor detecting devices.

4. A system as claimed in claim 3, wherein:
said semiconductor detecting devices are each adapted to passively detect said charge of said component without a portion of said semiconductor device binding with said component or chemically reacting with said component.

5. A system for detecting at least one polymer, comprising:
at least one semiconductor device having at least one detecting region having an opening through which said polymer can pass, said opening having a cross-sectional dimension of less than about 100 nm and being configured such that while said at least one polymer passes through said opening, a charge of at least a component of said polymer creates image charges in said region, said image charges being sufficient to increase the conductivity of said region by an amount related to said charge of said component, such that said detecting region is adapted to detect said charge of said component in said opening, wherein said detecting region includes an oxide layer defining said opening, said oxide layer including at least one silicon nanocrystal.

* * * * *